United States Patent [19]

Willms et al.

[11] Patent Number: 5,015,284

[45] Date of Patent: May 14, 1991

[54] ALKYL- AND ALKENYLSULFONYLUREAS WHICH ARE SUBSTITUTED IN THE HETEROCYCLE, AND THEIR USE AS HERBICIDES OR PLANT GROWTH REGULATORS

[75] Inventors: Lothar Willms, Hillschild; Klaus Bauer, Hanau; Hermann Bieringer, Eppstein/Taunus; Helmut Bürstell, Frankfurt am Main, all of Fed. Rep. of Germany

[73] Assignee: Hoechst Aktiengesellschaft, Frankfurt am Main, Fed. Rep. of Germany

[21] Appl. No.: 334,695

[22] Filed: Apr. 6, 1989

[30] Foreign Application Priority Data

Apr. 8, 1988 [DE] Fed. Rep. of Germany ....... 3811777

[51] Int. Cl.$^5$ .................. A01N 43/54; C07D 239/42; C07D 239/34; C07D 239/47; C07D 401/12; C07D 401/14; C07D 403/12; C07D 403/14

[52] U.S. Cl. ........................... 71/90; 71/92; 544/122; 544/320; 544/321; 544/123; 544/323; 544/327; 544/96; 544/332; 544/335; 544/58.6; 544/334; 544/54; 544/295; 544/296; 544/319; 544/324; 544/333; 544/331; 540/601; 540/544; 540/553; 540/575; 540/481; 540/470; 540/467

[58] Field of Search ...................... 71/90, 92; 544/122, 544/123, 96, 58.6, 54, 319, 324, 333, 331; 540/601, 575, 467

[56] References Cited

U.S. PATENT DOCUMENTS

| | | | |
|---|---|---|---|
| 4,419,121 | 12/1983 | Meyer et al. | 71/92 |
| 4,440,565 | 4/1984 | Willms et al. | 71/93 |
| 4,443,243 | 4/1984 | Fory et al. | 71/93 |
| 4,461,640 | 7/1984 | Levitt et al. | 71/92 |
| 4,492,598 | 1/1985 | Willms et al. | 71/93 |
| 4,680,053 | 7/1987 | Levitt et al. | 71/93 |
| 4,681,619 | 7/1987 | Meyer et al. | 71/92 |
| 4,693,741 | 9/1987 | Meyer et al. | 71/92 |
| 4,699,647 | 10/1987 | Rorer | 71/90 |
| 4,725,679 | 2/1988 | Willms | 540/546 |

FOREIGN PATENT DOCUMENTS

| | | |
|---|---|---|
| 11811/83 | 9/1983 | Australia. |
| 0044807 | 1/1982 | European Pat. Off. . |
| 0061661 | 10/1982 | European Pat. Off. . |
| 0070804 | 1/1983 | European Pat. Off. . |
| 0071958 | 2/1983 | European Pat. Off. . |
| 0085236 | 8/1983 | European Pat. Off. . |
| 0085276 | 8/1983 | European Pat. Off. . |
| 0087780 | 9/1983 | European Pat. Off. . |
| 0139947 | 5/1985 | European Pat. Off. . |
| 2110691 | 6/1983 | United Kingdom. |

OTHER PUBLICATIONS

*Agrochemical Service* of Wood Mackenzie & Co., Ltd., p. 32 (1988).

Andre Le Berre, André e Etienne et Bernard Desmazières, No. 150. Acides α-Sulfocarboxyliques et deérivées. V.—Sulfamoylacrboxyesters et carboxamides acycliques. Thiazetidine-1,2 one-3 dioxydes-1,1, Bulletin de la Societe Chimique de France 1975, No. 3-4, pp. 807-811.

*Primary Examiner*—John M. Ford
*Attorney, Agent, or Firm*—Curtis, Morris & Safford

[57] ABSTRACT

Compounds of the formula I, their stereoisomers or their salts $$\underset{SO_2-NH-\overset{Y}{\underset{\|}{C}}-\overset{R^2}{\underset{|}{N}}-R^3}{\overset{O}{\underset{A}{\overset{\|}{\diagdown}}}\hspace{-2pt}\diagup} \hspace{-4pt}X-R^1 \tag{I}$$

wherein

A denotes $>C(R^4)_2$ or $>C=C(R^5)_2$; $R^1$ denotes H, an optionally substituted aliphatic or cycloaliphatic radical, forfuryl, tetrahydrofurfuryl or (substituted) phenyl; $R^2$ denotes H, alkyl, alkenyl, alkynyl or alkoxy; $R^3$ denotes a radical of the formulae X denotes O, S or $NR^{12}$ and Y denotes O or S, possess excellent herbicidal and plant-growth regulating properties.

6 Claims, No Drawings

ALKYL- AND ALKENYLSULFONYLUREAS WHICH ARE SUBSTITUTED IN THE HETEROCYCLE, AND THEIR USE AS HERBICIDES OR PLANT GROWTH REGULATORS

It has been disclosed that alk(en)ylsulfonylureas which are substituted in the heterocycle show herbicidal and plant-growth regulating properties (see EP-A 061,661; EP-A 071,958; EP-A 085,236; EP-A 0,139,947). However, some of these show disadvantages on their application, for example a higher persistence, or unsatisfactory selectivity in important crops.

Novel heterocyclic sulfonyl ureas having advantageous herbicidal properties have now been found.

The present invention therefore relates to the compounds of the formula (I) or their stereoisomers

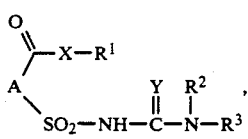

wherein

A denotes a radical of the formula $>C(R^4)_2$ or $>C=C(R^5)_2$, $R^1$ denotes H, $(C_1-C_8)$alkyl, $(C_2-C_8)$alkenyl, $(C_2-C_8)$alkynyl, it being possible for these aliphatic radicals to be monosubstituted or polysubstituted by halogen, or to be monosubstituted or disubstituted by $(C_1-C_6)$alkoxy, $(C_2-C_6)$alkenyloxy, $(C_2-C_6)$alkynyloxy, $(C_1-C_6)$alkylthio, $(C_1-C_6)$alkylsulfinyl, $(C_1-C_6)$alkylsulfonyl, $(C_1-C_6)$alkoxycarbonyl or by phenyl; $(C_3-C_8)$cycloalkyl which can be monosubstituted or polysubstituted by halogen, or monosubstituted or disubstituted by $(C_1-C_4)$alkoxy or $(C_1-C_4)$alkylthio; $(C_5-C_8)$cycloalkenyl, cyclopropylmethyl, epoxypropyl, furfuryl, tetrahydrofurfuryl, or phenoxy$(C_1-C_6)$alkyl or phenyl, both of which can be substituted in the phenyl ring by halogen, $(C_1-C_4)$alkyl, $(C_1-C_4)$alkoxy or $NO_2$, $R^2$ denotes H, $(C_1-C_8)$alkyl, $(C_2-C_8)$alkenyl, $(C_2-C_8)$alkynyl or $(C_1-C_4)$alkoxy, $R^3$ denotes a radical of the formula

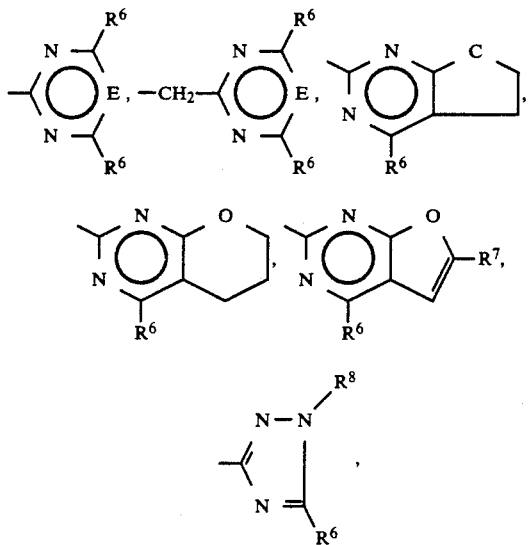

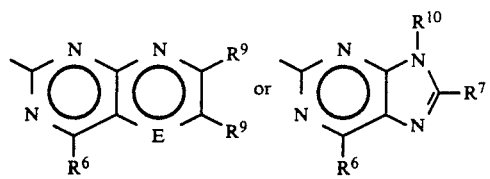

the $R^4$ radicals independently of one another denote H, $(C_1-C_6)$alkyl, $(C_2-C_6)$alkenyl, $(C_2-C_6)$-alkynyl, $(C_3-C_8)$cycloalkyl, it being possible for the abovementioned radicals which contain C to be monosubstituted or polysubstituted by halogen or monosubstituted or disubstituted by $(C_1-C_6)$alkoxy, $(C_2-C_6)$alkenyloxy, $(C_2-C_6)$alkynyloxy, $(C_1-C_6)$alkylthio, $(C_1-C_6)$alkylsulfinyl, $(C_1-C_6)$alkylsulfonyl or $(C_1-C_6)$alkoxycarbonyl, or by phenyl which can be monosubstituted or polysubstituted by halogen, $(C_1-C_4)$alkyl, $(C_1-C_4)$alkoxy, $(C_1-C_4)$alkylthio, $(C_1-C_4)$alkoxycarbonyl or $NO_2$, it being furthermore possible for one of the two radicals $R^4$ to denote phenyl which can be monosubstituted or polysubstituted by halogen, $(C_1-C_4)$alkyl, $(C_1-C_4)$alkoxy, $NO_2$ or $CF_3$, or for the two radicals $R^4$ together to denote an alkylene radical $-(CH_2)_m-$, the $R^5$ radicals independently of one another denote H, or $(C_1-C_6)$alkyl, which can be monosubstituted or polysubstituted by halogen or monosubstituted or disubstituted by $(C_1-C_6)$alkoxy, $(C_1-C_6)$alkylthio, $(C_1-C_6)$alkylsulfinyl or $(C_1-C_6)$alkoxycarbonyl, or it being possible for one of the radicals $R^5$ to denote phenyl which can be monosubstituted or polysubstituted by halogen, $(C_1-C_4)$alkyl, $(C_1-C_4)$alkoxy, $NO_2$, $CF_3$ or $(C_1-C_6)$alkoxycarbonyl, or for the two radicals $R^5$ together to denote an alkylene radical $-(CH_2)_n-$, the $R^6$ radicals independently of one another denote H, halogen, or $(C_1-C_6)$alkyl, $(C_1-C_6)$alkoxy or $(C_1-C_6)$alkylthio which can be monosubstituted or polysubstituted by halogen or monosubstituted or disubstituted by $(C_1-C_4)$alkoxy or $(C_1-C_4)$alkylthio; a radical $N(R^{11})_2$, $(C_3-C_6)$cycloalkyl, $-OCHR^7COOR^{11}$, $(C_3-C_5)$alkenyl, $(C_2-C_4)$alkynyl, $(C_3-C_5)$alkenyloxy or $(C_3-C_5)$alkynyloxy, $R^7$ denotes H or $(C_1-C_4)$alkyl, $R^8$ denotes $(C_1-C_4)$alkyl, $-CHF_2$ or $-CH_2CF_3$, the $R^9$ radicals independently of one another denote H, $(C_1-C_4)$alkyl, $(C_1-C_4)$alkoxy or halogen, $R^{10}$ denotes H, $(C_1-C_4)$alkyl, $-CHF_2$ or $-CH_2CF_3$, the $R^{11}$ radicals independently of one another denote H, $(C_1-C_4)$alkyl, $(C_2-C_4)$alkenyl or $(C_3-C_4)$alkynyl, E denotes CH or N, G denotes $CH_2$ or O, X denotes O, S or $NR^{12}$, Y denotes O or S, $R^{12}$ denotes H, $(C_1-C_6)$alkyl, $(C_2-C_6)$alkenyl, $(C_2-C_6)$alkynyl, $(C_1-C_6)$alkoxy, or a radical of the formula

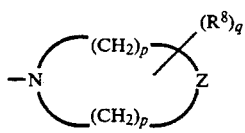

m denotes an integer from 2 to 6,
n denotes an integer from 3 to 6,
p denotes an integer from 1 to 3,
q denotes an integer from 0 to 3 and
Z denotes O, S, $CH_2$, NH or $N(C_1-C_4\text{-alkyl})$, or the salts thereof which can be employed in agriculture.

The compounds of the formula I can form salts in which the hydrogen of the $-SO_2-NH$ group is replaced by a cation which is suitable for agriculture. In general, these salts are metal salts, in particular alkali metal salts or alkaline earth metal salts, (optionally alkylated) ammonium salts or organic amine salts. They are preferably prepared from the compounds of the formula I in inert solvents, for example water, methanol or acetone, at temperatures from 0°–100° C. Examples of suitable bases for the preparation of the salts according to the invention are alkali metal carbonates, such as potassium carbonate, alkali metal hydroxides and alkaline earth metal hydroxides, ammonia or ethanolamine.

Preferred compounds of the formula I are those in which

A denotes a radical $>C(R^4)_2$ or $>C=C(R^5)_2$, $R^1$ denotes $(C_1-C_4)$alkyl which can be monosubstituted or polysubstituted by halogen or monosubstituted to disubstituted by $(C_1-C_4)$alkoxy, in particular $(C_1-C_4)$alkyl, $R^2$ denotes H, $(C_1-C_4)$alkyl or allyl, in particular H, $R^3$ denotes a radical of the formula

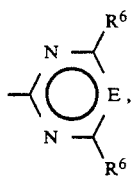

the $R^4$ radicals independently of one another denote H, or $(C_1-C_6)$ alkyl which can optionally be monosubstituted or polysubstituted by halogen or monosubstituted to disubstituted by $(C_1-C_4)$alkoxy or $(C_1-C_4)$alkylthio, or a radical $R^4$ denotes $(C_2-C_6)$alkenyl or phenyl which can be substituted as indicated above; a radical $R^4$ in particular denotes $(C_1-C_4)$alkyl or phenyl which is monosubstituted to trisubstituted by fluorine, chlorine, $(C_1-C_4)$alkoxy, $(C_1-C_4)$alkyl or nitro, and the other radical $R^4$ denotes hydrogen, the $R^5$ radicals independently of one another denote H, or $(C_1-C_6)$alkyl which can optionally be monosubstituted or polysubstituted by halogen, the $R^6$ radicals independently of one another denote halogen, or $(C_1-C_4)$alkyl or $(C_1-C_4)$alkoxy, both of which can be halogenated, in particular the radicals $CH_3$, $OCH_3$, $OC_2H_5$, Cl, $OCF_2H$, E denotes CH or N, X denotes O, S or $NR^{12}$, Y denotes O or S and $R^{12}$ denotes H, $(C_1-C_4)$alkyl or $(C_2-C_4)$alkenyl.

Halogen in particular denotes F, Cl or Br. Halogenated $(C_1-C_4)$alkyl or $(C_1-C_4)$alkoxy in particular denote $CF_3$, $CHF_2$, $CH_2CH_2Cl$, $CH_2CH_2Br$, $CF_2CFClH$, $CH_2CF_3$, $CH_2CCl_3$, $CF_2CHF_2$, $CF_2CHFCF_3$, $CH_2CH_2CH_2Cl$, $OCF_3$, $OCF_2H$, $OCH_2CF_3$, $OCH_2CH_2Cl$.

The present invention furthermore relates to processes for the preparation of compounds of the general formula (I) or their salts, which comprises reacting (a) a compound of the formula (II)

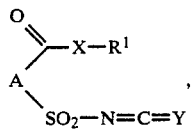 (II)

where A, X, Y, $R^1$ have the abovementioned meaning, with the exception that $R^1$ is not H and X is not NH, with the compound of the formula (III)

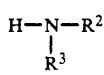 (III)

(b) a compound of the formula (IV)

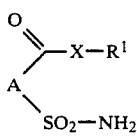 (IV)

with a (thio)carbamate of the formula (V)

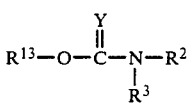 (V)

where $R^{13}$ denotes $(C_1-C_6)$alkyl, $(C_1-C_4)$haloalkyl or phenyl which can be monosubstituted or polysubstituted by halogen, $(C_1-C_4)$alkyl or $NO_2$, (c) a (thio)carbamate of the formula (VI) with a compound of the formula (III)

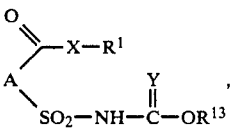 (VI)

where $R^{13}$ has the abovementioned meaning, or (d) a carboxylic acid of the formula (VII)

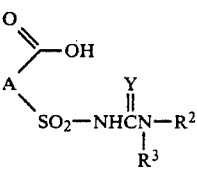 (VII)

with an alkylating reagent of the formula (VIII)

 (VIII)

where X represents a nucleofugic leaving group, for example halogen, alkyl-SO₂—O— or tosyl, and, if appropriate, converting the resulting compounds to their salts.

The compounds of the formulae (II) and (III) are preferably reacted in inert aprotic solvents, for example acetonitrile, dichloromethane, toluene, tetrahydrofuran or dioxane, at temperatures between 0° C. and the boiling point of the solvent.

The alkylsulfonyl iso(thio)cyanates of the formula (II) can be prepared in a simple manner from the corresponding sulfonamides of the formula (IX) by processes known in principle

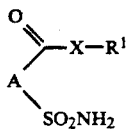

(IX)

(cf., for example, EP-A 085,276).

The sulfonamides of the formula (IX) are known or can be prepared by processes which are known in principle, for example by reacting aliphatic α-chlorosulfonylcarboxylic acid esters with ammonia (Bull. Soc. Chim. France 1975, 807).

The starting materials of the formula (III) are known or can be prepared by processes which are known in principle, for example by cyclizing corresponding guanidine derivates with appropriately substituted 1,3-diketones, cf., for example, "The Chemistry of Heterocyclic Compounds", Vol. XVI (1962) and Supplement I (1970), or by derivatization of cyanuric chloride, cf., for example, "The Chemistry of Heterocyclic Compounds", L. Rapaport: "s-Triazines and Derivates" (1959).

Preferably, the compound (IV) is reacted with the heterocyclic carbamates of the formula (V) in the presence of tertiary organic bases, for example 1,8-diazabicyclo-5,4,0-undec-7-ene (DBU) in inert solvents, such as acetonitrile or dioxane, at temperatures between 20° C. and the boiling point of the solvent (analogously to EP-A 44,807).

The carbamates (V) which are required for this are known from the literature or are prepared by known processes (EP-A 70,804).

The carbamates of the formula (VI) are novel and can be prepared by reacting compounds of the formula (IX) with corresponding chloroformic acid esters (see EP-A 87,780).

Preferably, the (thio)carbamates (VI) are reacted with the aminoheterocycles in inert solvents, for example toluene, xylene, chlorobenzene, dioxane or acetonitrile, at temperatures between 20° C. and the boiling point of the solvent in question.

The carboxylic acids (VII) are reacted with the reagents of the formula (VIII) in inert solvents, for example dimethylformamide or dimethyl sulfoxide, preferably in the presence of an auxiliary base, for example triethylamine or tetramethylammonium hydroxide pentahydrate, at temperatures between 0° C. and the boiling point of the solvent.

The sulfonyl ureas of the formula I which contain one or more asymmetric carbon atoms in the aliphatic radical A are present in enantiomeric or diastereomeric forms. In general, the corresponding compounds according to the invention are obtained as racemates or as mixtures of diastereomers. If desired, the customary techniques for separating these mixtures into the sterically uniform constituents can be applied. It is also possible to obtain the mentioned compounds in the pure form by using sterically uniform starting materials.

Furthermore, sulfonylureas of the formula I which contain one or more double bonds in the aliphatic radical A can occur as E or as Z isomers when they are olefinically substituted accordingly, and it is also possible to obtain these in the pure form, or to separate them. If, for example, unsaturated sulfonyl isocyanates of the general formula II are employed as E or Z isomers, the unsaturated sulfonyl ureas of the formula I are obtained in the sterically uniform form.

The formula I therefore embraces all abovementioned enantiomeric and diastereomeric forms of the compounds defined above.

The compounds according to the invention exhibit an excellent herbicidal activity against a broad range of economically important monocotyledon and dicotyledon noxious plants. The active substances also have a good effect on perennial weeds which produce shoots from rhizomes, small root stocks or other perennial organs and which are difficult to control. In this context, it is immaterial whether the substances are applied before sowing, or as a pre-emergence or post-emergence treatment. The following representatives of the monocotyledon and dicotyledon weed flora which can be controlled using the compounds according to the invention may be mentioned individually by way of example, without this representing any limitation on certain species.

On the side of the monocotyledon weed species, the compound has a good effect on, for example, Avena, Lolium, Alopecurus, Phalaris, Echinochloa, Digitaria, Setaria etc. and Cyperus species from the annual group and on the side of the perennial species Agropyron, Cynodon, Imperata and Sorghum etc. and also perennial Cyperus species. In the case of the dicotyledon weed species, the range of action embraces Galium, Viola, Veronica, Lamium, Stellaria, Amaranthus, Sinapis, Ipomoea, Matricaria, Abutilon, Sida etc. on the annual side, and Convolvulus, Cirsium, Rumex, Artemisia etc. in the case of the perennial weeds. Weeds which occur under the specific culture conditions of rice, for example, Sagittaria, Alisma, Eleocharis, Scirpus, Cyperus etc. are also controlled by the active substances according to the invention in an excellent manner.

If the compounds according to the invention are applied to the soil surface before germination, the emergence of the weed seedlings is either prevented completely, or the weeds grow until they have reached the cotyledon stage, but growth then ceases and eventually they die completely after three to four weeks after that.

When, in the post-emergence method, the active substances are applied to the green parts of the plants, growth also stops drastically very soon after the treatment, and the weed plants remain in the growth stage of the point in time of application, or they die more or less rapidly after a certain time, so that, in this manner, competition by weeds which is detrimental to the crop plants can be eliminated very early with a lasting effect by applying the novel agents according to the invention.

Even though the compounds according to the invention show an excellent herbicidal activity against monocotyledon and dicotyledon weeds, crop plants of economically important crops, for example wheat, barley, rye, rice, maize, sugar beet, cotton and soya beans, are damaged to a negligible extent only, or not at all. For these reasons, the present compounds are very suitable for selectively controlling undesired plant growth in agricultural plantations.

In addition, the compounds according to the invention show growth-regulating properties in crop plants. They engage in the plant metabolism in a regulating manner, and can therefore be employed for facilitating the harvest, for example by causing desiccation, abscission and reduced growth. Furthermore, they are also suitable for generally influencing and inhibiting undesired vegetative growth, without simultaneously destroying the plants. Inhibition of vegetative growth is an important factor in many monocotyledon and dicotyledon crops, since lodging can be reduced or prevented completely.

The agents according to the invention can be employed in the customary formulations as wettable powders, emulsifiable concentrates, emulsions, sprayable solutions, dusting agents, agents for seed treatment, dispersions, granules or microgranules.

Wettable powders are preparations which are uniformly dispersible in water and which, besides the active substance, also contain wetting agents, for example polyoxethylated alkylphenols, polyoxethylated fatty alcohols, alkyl- or alkylphenylsulfonates, and dispersing agents, for example sodium ligninsulfonate, sodium 2,2'-dinaphthylmethane-6,6'-disulfonate, sodium dibutylnaphthalenesulfonate or sodium oleoylmethyltaurinate, and, if appropriate, a diluent or inert substance. The preparations are prepared in a customary manner, for example by grinding and mixing the components.

Emulsifiable concentrates can be prepared, for example, by dissolving the active substance in an inert organic solvent, for example butanol, cyclohexanone, dimethylformamide, xylene and also higher-boiling aromatics or hydrocarbons, with the addition of one or more emulsifiers. In the case of liquid active substances, the solvent proportion can also be omitted completely or partly. Examples of emulsifiers which can be used are: calcium salts of alkylarylsulfonic acid, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, fatty alcohol/propylene oxide/ethylene oxide condensation products, alkyl polyglycol ethers, sorbitan fatty acid esters, polyoxethylene sorbitan fatty acid esters or polyoxethylene sorbitol esters.

Dusting agents can be obtained by grinding the active substance with highly-dispersed, solid substances, for example talc, natural clays such as kaolin, bentonite, pyrophillite, or diatomaceous earth.

Granules can be prepared either by spraying the active substance on to adsorptive inert material in the form of granules, or by applying active substance concentrates on to the surface of carrier substances, such as sand, kaolinites or of inert material in the form of granules by means of binders, for example polyvinyl alcohol, sodium polyacrylate or alternatively mineral oils. It is also possible to prepare granules from suitable active substances in the manner which is customary for the preparation of fertilizer granules, if desired in a mixture of fertilizers.

For example, the active substance concentration in wettable powders is approximately 10 to 90% by weight, the remainder 100% by weight is composed of customary formulation constituents. In the case of emulsifiable concentrates, the active substance concentration can be approximately 5 to 80% by weight. Formulations in the form of dusts usually contain 5 to 20% by weight, sprayable solutions approximately 2 to 20% by weight. In the case of granules, the active substance content partly depends on whether the effective compound is present in the liquid or solid form, and which granulation auxiliaries, fillers etc. are used.

In addition, the active substance formulations mentioned may contain the adhesives, wetting agents, dispersing agents, emulsifiers, penetrants, solvents, fillers or carriers which are customary in each case.

These formulation types which have been mentioned above are described, for example, in:
Winnacker-Kuciihler, "Chemische Technologie" [Chemical Technology], Vol. 7, C. Hauser Verlag Munich, 4th ed. 1986; van Falkenberg, "Pesticides Formulations", Marcel Dekker N.Y., 2nd ed. 1972-73; K. Martens, "Spray Drying Handbook", 3rd ed. 1979, G. Goodwin Ltd. London.

The formulation auxiliaries which are to be used for these formulations (inert materials, emulsifiers, wetting agents, surfactants, solvents etc.) are described, for example, in Marschen, "Solvents Guide", 2nd ed., Interscience, N.Y. 1950; McCutcheon's, "Detergents and Emulsifiers Annual", MC Publ. Corp., Ridgewood N.J.; Sisley and Wood or "Encyclopedia of Surface Active Agents", Chem. Publ. Co. Inc., N.Y. 1964.

For application, the concentrates which are present in the commercially available form may be diluted in the customary manner, for example in the case of wettable powders, emulsifiable concentrates, dispersions and, in some cases, also in the case of microgranules, by means of water. Preparations in the form of dusts and granules and also sprayable solutions are usually not diluted any further with other inert substances before they are used.

The application rate required varies with external conditions, such as temperature, humidity and others. It can vary within wide limits, for example, between 0.005 and 10.0 kg/ha or more of active substance, however, it is preferably between 0.01 and 5 kg/ha.

If appropriate, mixtures or mixed formulations with other active substances, for example insecticides, acaricides, herbicides, fertilizers, growth regulators or fungicides, are also possible.

The invention is illustrated in more detail by the examples below.

Formulation examples

A. A dusting agent is obtained by mixing 10 parts by weight of active substance and 90 parts by weight of talc or inert substance, and comminuting the mixture in a hammer mill.

B. A wettable powder which is readily dispersible in water is obtained by mixing 25 parts by weight of active substance, 64 parts by weight of kaolin-containing quartz as inert substance, 10 part by weight of potassium ligninsulfonate and 1 part by weight of sodium oleoylmethyltaurinate as wetting and dispersing agent, and grinding the mixture in a pin disk mill.

C. A dispersion concentrate which is readily dispersible in water is obtained by mixing 20 parts by weight of active substance with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255° to more than 377° C.), and grinding the mixture in a ball mill to a fineness of less than 5 microns.

D. An emulsifiable concentrate is obtained from 15 parts by weight of active substance, 75 parts by weight of cyclohexanone as solvent and 10 parts by weight of oxethylated nonylphenol (10 EO) as emulsifier.

CHEMICAL EXAMPLES

Example 1

D,L-N-[4,6-dimethoxy-pyrimidin-2-yl)aminocarbonyl]-(1-ethoxycarbonyl-eth-1-yl)sulfonamide 8.54 g (0.03 mol) of O-phenyl N-(4,6-dimethoxypyrimidin-2-yl)carbamate and 5.44 g (0.03 mol) of D,L-ethyl 2-aminosulfonylpropanoate (prepared in accordance with J. Org. Chem. 43, p. 4535 (1978)) are suspended in 200 ml of acetonitrile, and 5.02 g (0.033 mol) of DBU (DBU=1,8-diazabicyclo-5,4,0-undec-7-ene) are added at 20° C. After the reaction mixture has been stirred for 1 hour at 20° C., it is concentrated to approx. 50 ml, 200 ml of iced water are added, and a pH of approx. 3.5–4.5 is set using 2N HCl. After the reaction product has been filtered off with suction and recrystallized from ethyl acetate/n-hexane, 10.2 g (94% of theory) of D,L-N-[4,6-dimethoxypyrimidin-2-yl)aminocarbonyl]-(1-ethoxycarbonyl-eth-1-yl)sulfonamide of melting point 131°–133° C. are obtained.

Example 2

D-N-[4,6-dimethylpyrimidin-2-yl)aminocarbonyl]-(1-ethoxycarbonyl-eth-1-yl)sulfonamide (a) ethyl D-2-(tert. butylaminosulfonyl)propionate 22.8 g (0.2 mol) of benzylmercaptan are dissolved in 500 ml of anhydrous acetonitrile, and 9.6 g (0.2 mol) of NaH (50% strength) are slowly added at 0° C. Subsequently, stirring is continued for 2 hours at 25° C., and a solution of 21.7 g (0.2 mol) of ethyl L-2-chloropropionate in 100 ml of acetonitrile is added dropwise to the mixture at 0° C. The reaction mixture is allowed to react at room temperature for 1 hour and at 60° C. for 2 hours and is then filtered, the solvent is distilled of in vacuo, and the resulting oil is suspended at 0° C. in 250 ml of glacial acetic acid/200 ml of H₂O. The mixture is subsequently saturated with chlorine at 0° C., diluted with ice water and extracted with CH₂Cl₂, and the organic extracts are dried over Na₂SO₄. After the solvent has been distilled off in vacuo, a viscous oil is obtained which is dissolved in CH₂Cl₂, and the solution is reacted at 0° C. with 29.2 g (0.4 mol) of tert.butylamine. The mixture is allowed to react for 1 hour at room temperature and is diluted with ice water, and the sulfonamide is subsequently extracted using CH₂Cl₂. The mixture is dried over Na₂SO₄, the solvent is evaporated off, and the residue is distilled under a high vacuum. 37.9 g (85%) of ethyl D-2-(tert.butylaminosulfonyl)propionate of melting point 75°–76° C. are obtained (ee approx. 92%).

(b) Ethyl D-2-(aminosulfonyl)propionate 23.7 g (0.1 mol) of ethyl D-2-(tert.butylaminosulfonyl)propionate (Example 2a) are added to 100 ml of trifluoroacetic acid, and the mixture is refluxed for approx. 1 hour. It is then concentrated under a high vacuum, and the residue is recrystallized from isopropanol. 17.5 g (97% of theory) of ethyl D-2-(aminosulfonyl)propionate of melting point 72°–74° C. are obtained.

(c) Ethyl D-2-[(n-butylaminocarbonyl)aminosulfonyl]propionate 18.13 g (0.1 mol) of ethyl D-2-(aminosulfonyl)propionate were dissolved in 300 ml of acetone, 10.59 g (0.12 mol) of K₂CO₃ were added, and the mixture was stirred at 50° C. for 30 minutes. 11.9 g (0.1 mol) of n-butylisocyanate were subsequently added dropwise at room temperature; the suspension is stirred at 50° C. for 5 hours. After the solvent has been distilled off, the residue remaining is dissolved in water, the mixture is filtered, and the filtrate is acidified at 0° C. After the solvents have been distilled off, the remaining residue is dissolved in water, filtered and the filtrate acidified at 0° C. After the residue has been filtered off with suction and dried, 23.8 g (85% of theory) of ethyl D-2-[(n-butylaminocarbonyl)aminosulfonyl]propionate of melting point 66°–68° C. are obtained.

(d) D-(1-ethoxycarbonyleth-1-yl)sulfonyl isocyanate 19.63 g (0.07 mol) of ethyl D-2-[(n-butylaminocarbonyl)aminosulfonyl]propionate of Example 2c are suspended in 150 ml of xylene; phosgene is then passed in at 130° C. for approx. 2 hours. After the solvent has been distilled off, the desired sulfonyl isocyanate is obtained in quantitative yield (14.5 g), IR: NCO band at 2323 cm$^{-1}$).

(e) D-N-[(4,6-dimethoxypyrimidin-2-yl)aminocarbony]-(1-ethoxycarbonyleth-1-yl)sulfonamide 3.1 g (0.02 mol) of 2-amino-4,6-dimethoxypyrimidin are dissolved in 50 ml of CH₂Cl₂, and 4.67 g (0.0225 mol) of D-(1-ethoxycarbonyleth-1-yl)sulfonyl isocyanate are added at 0° C. The mixture is stirred at room temperature for 2 hours, the solvent is then distilled off, and the product remaining is recrystallized from ethyl acetate/n-hexane. 6.92 g (96% of theory) of D-N-[(4,6-dimethoxypyrimidin-2-yl)aminocarbonyl]-(1-ethoxycarbonyleth-1-yl)sulfonamide of melting point 134°–136° C. are obtained.

Example 3

Ethyl 2-{N-[N-(4,6-dimethoxypyrimidin-2-yl)aminocarbonyl]aminosulfonyl}-3-phenylprop-2-enoate (a) Ethyl 3-phenyl-2-(tert.butylaminosulfonyl)prop-2-enoate 11.2 g (0.05 mol) of ethyl 2-(tert.butylaminosulfonyl)acetate (see J. Org. Chem. 43, p. 4535 (1978)) are dissolved in 50 ml of benzaldehyde, 2 g of ammonium acetate and 2 ml of glacial acetic acid are added, and the mixture is stirred for 2 hours at 60° C. under a water pump vacuum (20 mm). The excess aldehyde is subsequently distilled off, and the residue is digested using n-hexane and recrystallized from isopropanol. 11.2 g (72% of theory) of ethyl 3-phenyl-2-(tert.butylaminosulfonyl)prop-2-enoate of melting point 111°–113° C. are obtained.

(b) Ethyl 3-phenyl-2-aminosulfonylprop-2-enoate 6.23 g (0.02 mol) of ethyl 3-phenyl-2-(tert.butylaminosulfonyl)prop-2-enoate (Example 3a) are heated in 50 ml of trifluoroacetic acid for 1 hour. Working-up in analogy to Example 2b) results in 4.1 g of ethyl 3-phenyl-2-aminosulfonylprop-2-enoate of melting point 88°–89° C.

(c) Ethyl 2-{N-[N-(4,6-dimethoxypyrimidin-2-yl)aminocarbonyl]aminosulfonyl}-3-phenylprop-2-enoate 5.10 g (0.02 mol) of ethyl (3-phenyl-2-aminosulfonyl)-prop-2-ene-carboxylate of Example 3b) are reacted in analogy to Example 1 with O-phenyl N-(4,6-dimethoxypyrimidin-2-yl) carbamate. 7.41 g (85% of theory) of ethyl 2-{N-[N-(4,6-dimethoxypyrimidin-2-yl)aminocarbonyl]aminosulfonyl}-3-phenylprop-2-enoate of melting point 140°–143° C. are obtained.

The compounds listed in Table 1 to 3 are prepared in analogy with the processes described in Example 1 to 3.

TABLE 1

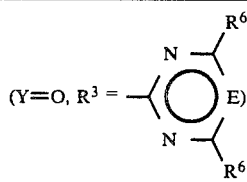

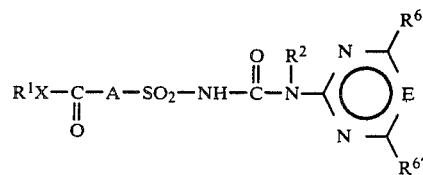

| Example No. | A | XR$^1$ | R$^2$ | R$^6$ | R$^{6'}$ | E | M.p. [°C.] |
|---|---|---|---|---|---|---|---|
| 4 | CH$_2$ | OCH$_3$ | H | CH$_3$ | CH$_3$ | CH | 164–166 |
| 5 | CH$_2$ | OCH$_3$ | H | OCH$_3$ | CH$_3$ | CH | |
| 6 | CH$_2$ | OCH$_3$ | H | OCH$_3$ | OCH$_3$ | CH | 142–143 |
| 7 | CH$_2$ | OCH$_3$ | H | OCH$_3$ | Cl | CH | |
| 8 | CH$_2$ | OH | H | CH$_3$ | CH$_3$ | CH | 178–180 |
| 9 | CH$_2$ | OCH$_3$ | H | OCHF$_2$ | OCH$_3$ | CH | |
| 10 | CH$_2$ | OCH$_3$ | H | OCHF$_2$ | OCHF$_2$ | CH | |
| 11 | CH$_2$ | OCH$_3$ | H | OCH$_2$CF$_3$ | OCH$_3$ | CH | |
| 12 | CH$_2$ | OCH$_3$ | H | CH$_3$ | Cl | CH | |
| 13 | CH$_2$ | OCH$_3$ | H | CH$_3$ | CH$_3$ | N | |
| 14 | CH$_2$ | OCH$_3$ | H | OCH$_3$ | CH$_3$ | N | 118–119 |
| 15 | CH$_2$ | OCH$_3$ | H | OCH$_3$ | OCH$_3$ | N | |
| 16 | CH$_2$ | OC$_2$H$_5$ | H | CH$_3$ | CH$_3$ | CH | 170 |
| 16 | CH$_2$ | OC$_2$H$_5$ | H | CH$_3$ | CH$_3$ | CH | 170 |
| 17 | CH$_2$ | OC$_2$H$_5$ | H | OCH$_3$ | CH$_3$ | CH | |
| 18 | CH$_3$ | OC$_2$H$_5$ | H | OCH$_3$ | OCH$_3$ | CH | |
| 19 | CH$_2$ | OC$_2$H$_5$ | H | OCH$_3$ | OCH$_3$ | CH | |
| 20 | CH$_2$ | OC$_2$H$_5$ | H | OCH$_3$ | Cl | CH | |
| 21 | CH$_2$ | OC$_2$H$_5$ | H | OCH$_3$ | NHCH$_3$ | CH | |
| 22 | CH$_2$ | OC$_2$H$_5$ | H | OCH$_3$ | Br | CH | |
| 23 | CH$_2$ | OC$_2$H$_5$ | H | OCH$_3$ | SCH$_3$ | CH | |
| 24 | CH$_2$ | OC$_2$H$_5$ | H | OCHF$_2$ | OCH$_3$ | CH | |
| 25 | CH$_2$ | OC$_2$H$_5$ | H | OCH$_3$ | CH$_3$ | N | |
| 26 | CH$_2$ | OC$_2$H$_5$ | H | OC$_2$H$_5$ | NHCH$_3$ | N | |
| 27 | CH$_2$ | OC$_2$H$_5$ | H | OCH$_3$ | N(CH$_3$)$_2$ | N | |
| 28 | CH$_3$—CH | OCH$_3$ | H | CH$_3$ | CH$_3$ | CH | 136–138 |
| 29 | CH$_3$—CH | OCH$_3$ | H | OCH$_3$ | CH$_3$ | CH | |
| 30 | CH$_3$—CH | OCH$_3$ | H | OCH$_3$ | OCH$_3$ | CH | |
| 31 | CH$_3$—CH | OCH$_3$ | CH$_3$ | OCH$_3$ | CH$_3$ | CH | |
| 32 | CH$_3$—CH | OCH$_3$ | H | OCH$_3$ | Cl | CH | 128–130 |
| 33 | CH$_3$—CH | OCH$_3$ | H | OCHF$_2$ | OCHF$_2$ | CH | |
| 34 | CH$_3$—CH | OCH$_3$ | H | SCH$_3$ | CH$_3$ | CH | |
| 35 | CH$_3$—CH | OCH$_3$ | H | CH(OCH$_3$)$_2$ | OCH$_3$ | CH | |
| 36 | CH$_3$—CH | OCH$_3$ | H | OCH$_3$ | CH$_3$ | N | |
| 37 | CH$_3$—CH | OCH$_3$ | H | OCH$_3$ | OCH$_3$ | N | |
| 38 | CH$_3$—CH | OCH$_3$ | H | NH$_2$ | OCH$_3$ | N | |
| 39 | CH$_3$—CH | OCH$_3$ | CH$_3$ | OCH$_3$ | CH$_3$ | N | |
| 40 (L) | CH$_3$—CH | OCH$_3$ | H | OCH$_3$ | OCH$_3$ | CH | 128–132 |
| 41 (L) | CH$_3$—CH | OCH$_3$ | H | OCH$_3$ | CH$_3$ | CH | |
| 42 (L) | CH$_3$—CH | OCH$_3$ | H | CH$_3$ | CH$_3$ | CH | |
| 43 (L) | CH$_3$—CH | OCH$_3$ | H | OCH$_3$ | CH$_3$ | N | |
| 44 (D) | CH$_3$—CH | OC$_2$H$_5$ | CH$_3$ | OCH$_3$ | OCH$_3$ | CH | |
| 45 (D) | CH$_3$—CH | OC$_2$H$_5$ | H | OCH$_3$ | Cl | CH | |
| 46 (D) | CH$_3$—CH | n-C$_3$H$_7$ | H | OCH$_3$ | Cl | CH | 148–149 |

TABLE 1-continued

| | | | | | | | |
|---|---|---|---|---|---|---|---|
| 47 | C$_2$H$_5$—CH | OCH$_3$ | H | CH$_3$ | CH$_3$ | CH | |
| 48 | C$_2$H$_5$—CH | OCH$_3$ | H | CH$_3$ | OCH$_3$ | CH | |
| 49 | C$_2$H$_5$—CH | OCH$_3$ | H | OCH$_3$ | OCH$_3$ | CH | 138–142 |
| 50 | C$_2$H$_5$—CH | OCH$_3$ | H | OCHF$_2$ | OCHF$_2$ | CH | |
| 51 | C$_2$H$_5$—CH | OCH$_3$ | H | OCHF$_2$ | OCH$_3$ | CH | |
| 52 | C$_2$H$_5$—CH | OCH$_3$ | H | OCH$_3$ | OCH$_2$CF$_3$ | CH | |
| 53 | C$_2$H$_5$—CH | OCH$_3$ | H | OC$_2$H$_5$ | OCH$_2$CF$_3$ | CH | |
| 54 | C$_2$H$_5$—CH | OCH$_3$ | H | OC$_2$H$_5$ | OC$_2$H$_5$ | CH | |
| 55 | C$_2$H$_5$—CH | OCH$_3$ | H | SCH$_3$ | CH$_3$ | CH | |
| 56 | C$_2$H$_5$—CH | OCH$_3$ | H | OCH$_3$ | NHCH$_3$ | CH | |
| 57 | C$_2$H$_5$—CH | OCH$_3$ | H | CH$_3$ | N(CH$_3$)$_2$ | CH | |
| 58 | C$_2$H$_5$—CH | OCH$_3$ | H | OCH$_3$ | | CH | |
| 59 | C$_2$H$_5$—CH | OCH$_3$ | H | CH$_3$ | | CH | |
| 60 | C$_2$H$_5$—CH | OCH$_3$ | H | OCHF$_2$ | OCHF$_2$ | CH | |
| 61 | C$_2$H$_5$—CH | OCH$_3$ | CH$_3$ | OCH$_3$ | OCH$_3$ | CH | |
| 62 | C$_2$H$_5$—CH | OCH$_3$ | CH$_3$ | CH$_3$ | CH$_3$ | CH | |
| 63 | C$_2$H$_5$—CH | OCH$_3$ | H | OCH$_3$ | OCH$_3$ | N | |
| 64 | C$_2$H$_5$—CH | OCH$_3$ | H | OCH$_3$ | CH$_3$ | N | 118 |
| 65 | C$_2$H$_5$—CH | OCH$_3$ | H | OCH$_3$ | SCH$_2$ | N | |
| 66 | C$_2$H$_5$—CH | OCH$_3$ | H | CH$_3$ | CH$_3$ | N | |
| 67 | C$_2$H$_5$—CH | OCH$_3$ | H | OC$_2$H$_5$ | OCH$_3$ | N | |
| 68 | C$_2$H$_5$—CH | OCH$_3$ | H | OCH$_3$ | NHCH$_3$ | N | |
| 69 | C$_2$H$_5$—CH | OCH$_3$ | H | OC$_2$H$_5$ | NHCH$_3$ | N | |
| 70 | C$_2$H$_5$—CH | OCH$_3$ | H | OCH$_3$ | NHC$_2$H$_5$ | N | |
| 71 | C$_2$H$_5$—CH | OCH$_3$ | H | OC$_2$H$_5$ | NHC$_2$H$_5$ | N | |
| 72 | C$_2$H$_5$—CH | OCH$_3$ | H | OCH$_3$ | N(CH$_3$)$_2$ | N | |
| 73 | C$_2$H$_5$—CH | OCH$_3$ | H | OC$_2$H$_5$ | N(CH$_3$)$_2$ | N | |
| 74 | C$_2$H$_5$—CH | OCH$_3$ | H | OCH$_3$ | ◁ | N | |
| 75 | C$_2$H$_5$—CH | OCH$_3$ | H | OCH$_3$ | OCH$_2$CF$_3$ | N | |
| 76 | C$_2$H$_5$—CH | OCH$_3$ | H | CH$_3$ | OCH$_2$CF$_3$ | N | |
| 77 | C$_2$H$_5$—CH | OCH$_3$ | CH$_3$ | OCH$_3$ | CH$_3$ | N | 78–86 |
| 78 | C$_2$H$_5$—CH | OCH$_3$ | CH$_3$ | OCH$_3$ | OCH$_3$ | N | |
| 79 | C$_2$H$_5$—CH | OCH$_3$ | CH$_3$ | OCH$_3$ | NHCH$_3$ | N | |
| 80 | C$_2$H$_5$—CH | OCH$_3$ | H | OCH$_3$ | OCH$_3$ | CH | 48–50 |
| 81 | C$_2$H$_5$—CH | OCH$_3$ | H | OCH$_3$ | CH$_3$ | CH | |
| 82 (D) | C$_2$H$_5$—CH | OCH$_3$ | H | OCH$_3$ | OCH$_3$ | CH | 142–145 |
| 83 (D) | C$_2$H$_5$—CH | OCH$_3$ | H | CH$_3$ | OCH$_3$ | CH | |
| 84 (D) | C$_2$H$_5$—CH | OCH$_3$ | H | CH$_3$ | CH$_3$ | CH | |
| 85 (D) | C$_2$H$_5$—CH | OCH$_3$ | H | OCH$_3$ | Cl | CH | |
| 86 (D) | C$_2$H$_5$—CH | OCH$_3$ | H | OCHF$_2$ | OCHF$_2$ | CH | |
| 87 (D) | C$_2$H$_5$—CH | OCH$_3$ | H | OCHF$_2$ | OCH$_3$ | CH | |
| 88 (D) | C$_2$H$_5$—CH | OCH$_3$ | H | OCH$_3$ | OCH$_2$CF$_3$ | CH | |
| 89 (D) | C$_2$H$_5$—CH | OCH$_3$ | H | OC$_2$H$_5$ | OCH$_2$CF$_3$ | CH | |
| 90 (D) | C$_2$H$_5$—CH | OCH$_3$ | H | OC$_2$H$_5$ | OC$_2$H$_5$ | CH | |
| 91 (D) | C$_2$H$_5$—CH | OCH$_3$ | H | SCH$_3$ | CH$_3$ | CH | |
| 92 (D) | C$_2$H$_5$—CH | OCH$_3$ | H | OCH$_3$ | NHCH$_3$ | CH | |
| 93 (D) | C$_2$H$_5$—CH | OCH$_3$ | H | CH$_3$ | N(CH$_3$)$_2$ | CH | |
| 94 (D) | C$_2$H$_5$—CH | OCH$_3$ | H | OCH$_3$ | ◁ | CH | |
| 95 (D) | C$_2$H$_5$—CH | OCH$_3$ | H | CH$_3$ | ◁ | CH | |
| 96 (D) | C$_2$H$_5$—CH | OCH$_3$ | H | OCHF$_2$ | OCHF$_2$ | CH | |
| 97 (D) | C$_2$H$_5$—CH | OCH$_3$ | CH$_3$ | OCH$_3$ | OCH$_3$ | CH | |
| 98 (D) | C$_2$H$_5$—CH | OCH$_3$ | CH$_3$ | CH$_3$ | CH$_3$ | CN | |
| 99 (D) | C$_2$H$_5$—CH | OCH$_3$ | H | OCH$_3$ | OCH$_3$ | N | |
| 100 (D) | C$_2$H$_5$—CH | OCH$_3$ | H | OCH$_3$ | CH$_3$ | N | |

TABLE 1-continued

| | | | | | | | |
|---|---|---|---|---|---|---|---|
| 101 (D) | C$_2$H$_5$—CH | OCH$_3$ | H | OCH$_3$ | SCH$_2$ | N | |
| 102 (D) | C$_2$H$_5$—CH | OCH$_3$ | H | CH$_3$ | CH$_3$ | N | |
| 103 (D) | C$_2$H$_5$—CH | OCH$_3$ | H | OC$_2$H$_5$ | OCH$_3$ | N | |
| 104 (D) | C$_2$H$_5$—CH | OCH$_3$ | H | OCH$_3$ | NHCH$_3$ | N | |
| 105 (D) | C$_2$H$_5$—CH | OCH$_3$ | H | OC$_2$H$_5$ | NHCH$_3$ | N | |
| 106 (D) | C$_2$H$_5$—CH | OCH$_3$ | H | OCH$_3$ | NHC$_2$H$_5$ | N | |
| 107 (D) | C$_2$H$_5$—CH | OCH$_3$ | H | OC$_2$H$_5$ | NHC$_2$H$_5$ | N | |
| 108 (D) | C$_2$H$_5$—CH | OCH$_3$ | H | OCH$_3$ | N(CH$_3$)$_2$ | N | |
| 109 (D) | C$_2$H$_5$—CH | OCH$_3$ | H | OC$_2$H$_5$ | N(CH$_3$)$_2$ | N | |
| 110 (D) | C$_2$H$_5$—CH | OCH$_3$ | H | OCH$_3$ | ◁ | N | |
| 111 (D) | C$_2$H$_5$—CH | OCH$_3$ | H | OCH$_3$ | OCH$_2$CF$_3$ | N | |
| 112 (D) | C$_2$H$_5$—CH | OCH$_3$ | H | CH$_3$ | OCH$_2$CF$_3$ | N | |
| 113 (D) | C$_2$H$_5$—CH | OCH$_3$ | CH$_3$ | OCH$_3$ | CH$_3$ | N | |
| 114 (D) | C$_2$H$_5$—CH | OCH$_3$ | CH$_3$ | OCH$_3$ | OCH$_3$ | N | |
| 115 (D) | C$_2$H$_5$—CH | OCH$_3$ | CH$_3$ | OCH$_3$ | NHCH$_3$ | N | |
| 116 (D) | C$_2$H$_5$—CH | OCH$_3$ | H | OCH$_3$ | OCH$_3$ | CH | |
| 117 (D) | C$_2$H$_5$—CH | OCH$_3$ | H | OCH$_3$ | CH$_3$ | CH | |
| 118 (L) | C$_2$H$_5$—CH | OCH$_3$ | H | OCH$_3$ | OCH$_3$ | CH | |
| 119 (L) | C$_2$H$_5$—CH | OCH$_3$ | H | CH$_3$ | OCH$_3$ | CH | |
| 120 (L) | C$_2$H$_5$—CH | OCH$_3$ | H | CH$_3$ | CH$_3$ | CH | |
| 121 (L) | C$_2$H$_5$—CH | OCH$_3$ | H | OCH$_3$ | Cl | CH | |
| 122 (L) | C$_2$H$_5$—CH | OCH$_3$ | H | OCHF$_2$ | OCHF$_2$ | CH | |
| 123 (L) | C$_2$H$_5$—CH | OCH$_3$ | H | OCHF$_2$ | OCH$_3$ | CH | |
| 124 (L) | C$_2$H$_5$—CH | OCH$_3$ | H | OCH$_3$ | OCH$_2$CF$_3$ | CH | |
| 125 (L) | C$_2$H$_5$—CH | OCH$_3$ | H | OC$_2$H$_5$ | OCH$_2$CF$_3$ | CH | |
| 126 (L) | C$_2$H$_5$—CH | OCH$_3$ | H | OC$_2$H$_5$ | OC$_2$H$_5$ | CH | |
| 127 (L) | C$_2$H$_5$—CH | OCH$_3$ | H | SCH$_3$ | CH$_3$ | CH | |
| 128 (L) | C$_2$H$_5$—CH | OCH$_3$ | H | OCH$_3$ | NHCH$_3$ | CH | |
| 129 (L) | C$_2$H$_5$—CH | OCH$_3$ | H | CH$_3$ | N(CH$_3$)$_2$ | CH | |
| 130 (L) | C$_2$H$_5$—CH | OCH$_3$ | H | OCH$_3$ | | CH | |
| 131 (L) | C$_2$H$_5$—CH | OCH$_3$ | H | CH$_3$ | | CH | |
| 132 (L) | C$_2$H$_5$—CH | OCH$_3$ | H | OCHF$_2$ | OCHF$_2$ | CH | |
| 133 (L) | C$_2$H$_5$—CH | OCH$_3$ | CH$_3$ | OCH$_3$ | OCH$_3$ | CH | |
| 134 (L) | C$_2$H$_5$—CH | OCH$_3$ | CH$_3$ | CH$_3$ | CH$_3$ | CH | |
| 135 (L) | C$_2$H$_5$—CH | OCH$_3$ | H | OCH$_3$ | OCH$_3$ | N | |
| 136 (L) | C$_2$H$_5$—CH | OCH$_3$ | H | OCH$_3$ | CH$_3$ | N | 142–144 |
| 137 (L) | C$_2$H$_5$—CH | OCH$_3$ | H | OCH$_3$ | SCH$_2$ | N | |
| 138 (L) | C$_2$H$_5$—CH | OCH$_3$ | H | CH$_3$ | CH$_3$ | N | |
| 139 (L) | C$_2$H$_5$—CH | OCH$_3$ | H | OC$_2$H$_5$ | OCH$_3$ | N | |
| 140 (L) | C$_2$H$_5$—CH | OCH$_3$ | H | OCH$_3$ | NHCH$_3$ | N | |

TABLE 1-continued

| | | | | | | |
|---|---|---|---|---|---|---|
| 141 (L) | C₂H₅—CH | OCH₃ | H | OC₂H₅ | NHCH₃ | N |
| 142 (L) | C₂H₅—CH | OCH₃ | H | OCH₃ | NHC₂H₅ | N |
| 143 (L) | C₂H₅—CH | OCH₃ | H | OC₂H₅ | NHC₂H₅ | N |
| 144 (L) | C₂H₅—CH | OCH₃ | H | OCH₃ | N(CH₃)₂ | N |
| 145 (L) | C₂H₅—CH | OCH₃ | H | OC₂H₅ | N(CH₃)₂ | N |
| 146 (L) | C₂H₅—CH | OCH₃ | H | OCH₃ |  | N |
| 147 (L) | C₂H₅—CH | OCH₃ | H | OCH₃ | OCH₂CF₃ | N |
| 148 (L) | C₂H₅—CH | OCH₃ | H | CH₃ | OCH₂CF₃ | N |
| 149 (L) | C₂H₅—CH | OCH₃ | CH₃ | OCH₃ | CH₃ | N |
| 150 (L) | C₂H₅—CH | OCH₃ | CH₃ | OCH₃ | OCH₃ | N |
| 151 (L) | C₂H₅—CH | OCH₃ | CH₃ | OCH₃ | NHCH₃ | N |
| 152 (L) | C₂H₅—CH | OCH₃ | H | OCH₃ | OCH₃ | CH |
| 153 (L) | C₂H₅—CH | OCH₃ | H | OCH₃ | CH₃ | CH |
| 154 | C₂H₅—CH | OC₂H₅ | H | OCH₃ | OCH₃ | CH | 102–104 |
| 155 | C₂H₅—CH | OC₂H₅ | H | CH₃ | OCH₃ | CH |
| 156 | C₂H₅—CH | OC₂H₅ | H | CH₃ | CH₃ | CH |
| 157 | C₂H₅—CH | OC₂H₅ | H | OCH₃ | Cl | CH | 78–83 |
| 158 | C₂H₅—CH | OC₂H₅ | H | OCHF₂ | OCHF₂ | CH |
| 159 | C₂H₅—CH | OC₂H₅ | H | OCHF₂ | OCH₃ | CH |
| 160 | C₂H₅—CH | OC₂H₅ | H | OCH₃ | OCH₂CF₃ | CH |
| 161 | C₂H₅—CH | OC₂H₅ | H | OC₂H₅ | OCH₂CF₃ | CH |
| 162 | C₂H₅—CH | OC₂H₅ | H | OC₂H₅ | OC₂H₅ | CH |
| 163 | C₂H₅—CH | OC₂H₅ | H | SCH₃ | CH₃ | CH |
| 164 | C₂H₅—CH | OC₂H₅ | H | OCH₃ | NHCH₃ | CH |
| 165 | C₂H₅—CH | OC₂H₅ | H | CH₃ | N(CH₃)₂ | CH |
| 166 | C₂H₅—CH | OC₂H₅ | H | OCH₃ |  | CH |
| 167 | C₂H₅—CH | OC₂H₅ | H | CH₃ |  | CH |
| 168 | C₂H₅—CH | OC₂H₅ | H | OCHF₂ | OCHF₂ | CH |
| 169 | C₂H₅—CH | OC₂H₅ | CH₃ | OCH₃ | OCH₃ | CH |
| 170 | C₂H₅—CH | OC₂H₅ | CH₃ | CH₃ | CH₃ | CH |
| 171 | C₂H₅—CH | OC₂H₅ | H | OCH₃ | OCH₃ | N |
| 172 | C₂H₅—CH | OC₂H₅ | H | OCH₃ | CH₃ | N |
| 173 | C₂H₅—CH | OC₂H₅ | H | OCH₃ | SCH₂ | N |
| 174 | C₂H₅—CH | OC₂H₅ | H | CH₃ | CH₃ | N |
| 175 | C₂H₅—CH | OC₂H₅ | H | OC₂H₅ | OCH₃ | N |
| 176 | C₂H₅—CH | OC₂H₅ | H | OCH₃ | NHCH₃ | N |
| 177 | C₂H₅—CH | OC₂H₅ | H | OC₂H₅ | NHCH₃ | N |
| 178 | C₂H₅—CH | OC₂H₅ | H | OCH₃ | NHC₂H₅ | N |
| 179 | C₂H₅—CH | OC₂H₅ | H | OC₂H₅ | NHC₂H₅ | N |
| 180 | C₂H₅—CH | OC₂H₅ | H | OCH₃ | N(CH₃)₂ | N |
| 181 | C₂H₅—CH | OC₂H₅ | H | OC₂H₅ | N(CH₃)₂ | N |
| 182 | C₂H₅—CH | OC₂H₅ | H | OCH₃ |  | N |
| 183 | C₂H₅—CH | OC₂H₅ | H | OCH₃ | OCH₂CF₃ | N |
| 184 | C₂H₅—CH | OC₂H₅ | H | CH₃ | OCH₂CF₃ | N |
| 185 | C₂H₅—CH | OC₂H₅ | CH₃ | OCH₃ | CH₃ | N |
| 186 | C₂H₅—CH | OC₂H₅ | CH₃. | OCH₃ | OCH₃ | N |
| 187 | C₂H₅—CH | OC₂H₅ | CH₃ | OCH₃ | NHCH₃ | N |
| 188 | C₂H₅—CH | OC₂H₅ | H | OCH₃ | OCH₃ | CH |
| 189 | C₂H₅—CH | OC₂H₅ | H | OCH₃ | CH₃ | CH |
| 190 (L) | C₂H₅—CH | OC₂H₅ | H | OCH₃ | OCH₃ | CH |
| 191 (L) | C₂H₅—CH | OC₂H₅ | H | CH₃ | OCH₃ | CH |
| 192 | C₂H₅—CH | OC₂H₅ | H | CH₃ | CH₃ | CH |

TABLE 1-continued

| | | | | | | |
|---|---|---|---|---|---|---|
| 193 (L) | C₂H₅—CH | OC₂H₅ | H | OCH₃ | Cl | CH |
| 194 (L) | C₂H₅—CH | OC₂H₅ | H | OCHF₂ | OCHF₂ | CH |
| 195 (L) | C₂H₅—CH | OC₂H₅ | H | OCHF₂ | OCHF₂ | CH |
| 196 (L) | C₂H₅—CH | OC₂H₅ | H | OCH₃ | OCH₂CF₃ | CH |
| 197 (L) | C₂H₅—CH | OC₂H₅ | H | OC₂H₅ | OCH₂CF₃ | CH |
| 198 (L) | C₂H₅—CH | OC₂H₅ | H | OC₂H₅ | OC₂H₅ | CH |
| 199 (L) | C₂H₅—CH | OC₂H₅ | H | SCH₃ | CH₃ | CH |
| 200 (L) | C₂H₅—CH | OC₂H₅ | H | OCH₃ | NHCH₃ | CH |
| 201 (L) | C₂H₅—CH | OC₂H₅ | H | CH₃ | N(CH₃)₂ | CH |
| 202 (L) | C₂H₅—CH | OC₂H₅ | H | OCH₃ |  | CH |
| 203 (L) | C₂H₅—CH | OC₂H₅ | H | CH₃ |  | CH |
| 204 (L) | C₂H₅—CH | OC₂H₅ | H | OCHF₂ | OCHF₂ | CH |
| 205 (L) | C₂H₅—CH | OC₂H₅ | CH₃ | OCH₃ | OCH₃ | CH |
| 206 (L) | C₂H₅—CH | OC₂H₅ | CH₃ | CH₃ | CH₃ | CH |
| 207 (L) | C₂H₅—CH | OC₂H₅ | H | OCH₃ | OCH₃ | N |
| 208 (L) | C₂H₅—CH | OC₂H₅ | H | OCH₃ | CH₃ | N |
| 209 (L) | C₂H₅—CH | OC₂H₅ | H | OCH₃ | SCH₂ | N |
| 210 (L) | C₂H₅—CH | OC₂H₅ | H | CH₃ | CH₃ | N |
| 211 (L) | C₂H₅—CH | OC₂H₅ | H | OC₂H₅ | OCH₃ | N |
| 212 (L) | C₂H₅—CH | OC₂H₅ | H | OCH₃ | NHCH₃ | N |
| 213 (L) | C₂H₅—CH | OC₂H₅ | H | OC₂H₅ | NHCH₃ | N |
| 214 (L) | C₂H₅—CH | OC₂H₅ | H | OCH₃ | NHC₂H₅ | N |
| 215 (L) | C₂H₅—CH | OC₂H₅ | H | OC₂H₅ | NHC₂H₅ | N |
| 216 (L) | C₂H₅—CH | OC₂H₅ | H | OCH₃ | N(CH₃)₂ | N |
| 217 (L) | C₂H₅—CH | OC₂H₅ | H | OC₂H₅ | (CH₃)₂ | N |
| 218 (L) | C₂H₅—CH | OC₂H₅ | H | OCH₃ |  | N |
| 219 (L) | C₂H₅—CH | OC₂H₅ | H | OCH₃ | OCH₂CF₃ | N |
| 220 (L) | C₂H₅—CH | OC₂H₅ | H | CH₃ | OCH₂CF₃ | N |
| 221 (L) | C₂H₅—CH | OC₂H₅ | CH₃ | OCH₃ | CH₃ | N |
| 222 (L) | C₂H₅—CH | OC₂H₅ | CH₃ | OCH₃ | OCH₃ | N |
| 223 (L) | C₂H₅—CH | OC₂H₅ | CH₃ | OCH₃ | NHCH₃ | N |
| 224 (L) | C₂H₅—CH₃ | OC₂H₅ | H | OCH₃ | OCH₃ | CH |
| 225 (L) | C₂H₅—CH | OC₂H₅ | H | OCH₃ | CH₃ | CH |
| 226 (D) | C₂H₅—CH | OC₂H₅ | H | OCH₃ | OCH₃ | CH |
| 227 (D) | C₂H₅—CH | OC₂H₅ | H | CH₃ | OCH₃ | CH |
| 228 (D) | C₂H₅—CH | OC₂H₅ | H | CH₃ | CH₃ | CH |
| 229 | C₂H₅—CH | OC₂H₅ | H | OCH₃ | Cl | CH |

TABLE 1-continued

| | | | | | | | |
|---|---|---|---|---|---|---|---|
| 230 (D) | C$_2$H$_5$—CH | OC$_2$H$_5$ | H | OCHF$_2$ | OCHF$_2$ | CH | 182–184 |
| 231 (D) | C$_2$H$_5$—CH | OC$_2$H$_5$ | H | OCHF$_2$ | OCH$_3$ | CH | |
| 232 (D) | C$_2$H$_5$—CH | OC$_2$H$_5$ | H | OCH$_3$ | OCH$_2$CF$_3$ | CH | |
| 233 (D) | C$_2$H$_5$—CH | OC$_2$H$_5$ | H | OC$_2$H$_5$ | OCH$_2$CF$_3$ | CH | |
| 234 (D) | C$_2$H$_5$—CH | OC$_2$H$_5$ | H | OC$_2$H$_5$ | OC$_2$H$_5$ | CH | |
| 235 (D) | C$_2$H$_5$—CH | OC$_2$H$_5$ | H | SCH$_3$ | CH$_3$ | CH | |
| 236 (D) | C$_2$H$_5$—CH | OC$_2$H$_5$ | H | OCH$_3$ | NHCH$_3$ | CH | |
| 237 (D) | C$_2$H$_5$—CH | OC$_2$H$_5$ | H | CH$_3$ | N(CH$_3$)$_2$ | CH | |
| 238 (D) | C$_2$H$_5$—CH | OC$_2$H$_5$ | H | OCH$_3$ |  | CH | |
| 239 (D) | C$_2$H$_5$—CH | OC$_2$H$_5$ | H | CH$_3$ |  | CH | |
| 240 (D) | C$_2$H$_5$—CH | OC$_2$H$_5$ | H | OCHF$_2$ | OCHF$_2$ | CH | |
| 241 (D) | C$_2$H$_5$—CH | OC$_2$H$_5$ | CH$_3$ | OCH$_3$ | OCH$_3$ | CH | |
| 242 (D) | C$_2$H$_5$—CH | OC$_2$H$_5$ | CH$_3$ | CH$_3$ | CH$_3$ | CH | |
| 243 (D) | C$_2$H$_5$—CH | OC$_2$H$_5$ | H | OCH$_3$ | OCH$_3$ | N | |
| 244 (D) | C$_2$H$_5$—CH | OC$_2$H$_5$ | H | OCH$_3$ | CH$_3$ | N | |
| 245 (D) | C$_2$H$_5$—CH | OC$_2$H$_5$ | H | OCH$_3$ | SCH$_2$ | N | |
| 246 (D) | C$_2$H$_5$—CH | OC$_2$H$_5$ | H | CH$_3$ | CH$_3$ | N | |
| 247 (D) | C$_2$H$_5$—CH | OC$_2$H$_5$ | H | OC$_2$H$_5$ | OCH$_3$ | N | |
| 248 (D) | C$_2$H$_5$—CH | OC$_2$H$_5$ | H | OCH$_3$ | NHCH$_3$ | N | |
| 249 (D) | C$_2$H$_5$—CH | OC$_2$H$_5$ | H | OC$_2$H$_5$ | NHCH$_3$ | N | |
| 250 (D) | C$_2$H$_5$—CH | OC$_2$H$_5$ | H | OCH$_3$ | NHC$_2$H$_5$ | N | |
| 251 (D) | C$_2$H$_5$—CH | OC$_2$H$_5$ | H | OC$_2$H$_5$ | NHC$_2$H$_5$ | N | |
| 252 (D) | C$_2$H$_5$—CH | OC$_2$H$_5$ | H | OCH$_3$ | N(CH$_3$)$_2$ | N | |
| 253 (D) | C$_2$H$_5$—CH | OC$_2$H$_5$ | H | OC$_2$H$_5$ | N(CH$_3$)$_2$ | N | |
| 254 (D) | C$_2$H$_5$—CH | OC$_2$H$_5$ | H | OCH$_3$ |  | N | |
| 255 (D) | C$_2$H$_5$—CH | OC$_2$H$_5$ | H | OCH$_3$ | OCH$_2$CF$_3$ | N | |
| 256 (D) | C$_2$H$_5$—CH | OC$_2$H$_5$ | H | CH$_3$ | OCH$_2$CF$_3$ | N | |
| 257 (D) | C$_2$H$_5$—CH | OC$_2$H$_5$ | CH$_3$ | OCH$_3$ | CH$_3$ | N | |
| 258 (D) | C$_2$H$_5$—CH | OC$_2$H$_5$ | CH$_3$ | OCH$_3$ | OCH$_3$ | N | |
| 259 (D) | C$_2$H$_5$—CH | OC$_2$H$_5$ | CH$_3$ | OCH$_3$ | NHCH$_3$ | N | |
| 260 (D) | C$_2$H$_5$—CH | OC$_2$H$_5$ | H | OCH$_3$ | OCH$_3$ | CH | |
| 261 (D) | C$_2$H$_5$—CH | OC$_2$H$_5$ | H | OCH$_3$ | CH$_3$ | CH | |
| 262 | n-C$_3$H$_7$—CH | OC$_2$H$_5$ | H | CH$_3$ | CH$_3$ | CH | |
| 263 | n-C$_3$H$_7$—CH | OC$_2$H$_5$ | H | OCH$_3$ | CH$_3$ | CH | |
| 264 | n-C$_3$H$_7$—CH | OC$_2$H$_5$ | H | OCH$_3$ | OCH$_3$ | CH | 76–78 |
| 265 | n-C$_3$H$_7$—CH | OC$_2$H$_5$ | CH$_3$ | OCH$_3$ | OCH$_3$ | CH | |
| 266 | n-C$_3$H$_7$—CH | OC$_2$H$_5$ | H | OCH$_3$ | Cl | CH | |
| 267 | n-C$_3$H$_7$—CH | OC$_2$H$_5$ | H | OCH$_3$ | NHCH$_3$ | CH | |
| 268 | n-C$_3$H$_7$—CH | OC$_2$H$_5$ | H | OCH$_3$ | Br | CH | |
| 269 | n-C$_3$H$_7$—CH | OC$_2$H$_5$ | H | OCH$_3$ | SCH$_3$ | CH | |
| 270 | n-C$_3$H$_7$—CH | OC$_2$H$_5$ | H | OCHF$_2$ | OCH$_3$ | CH | |

TABLE 1-continued

| | | | | | | | |
|---|---|---|---|---|---|---|---|
| 271 | n-C$_3$H$_7$—CH | OC$_2$H$_5$ | H | OCH$_3$ | CH$_3$ | N | |
| 272 | n-C$_3$H$_7$—CH | OC$_2$H$_5$ | H | OC$_2$H$_5$ | NHCH$_3$ | N | |
| 273 | n-C$_3$H$_7$—CH | OC$_2$H$_5$ | H | OCH$_3$ | N(CH$_3$)$_2$ | N | |
| 274 | (CH$_3$)$_2$CH—CH | OC$_2$H$_5$ | H | CH$_3$ | CH$_3$ | CH | |
| 275 | (CH$_3$)$_2$CH—CH | OC$_2$H$_5$ | H | OCH$_3$ | CH$_3$ | CH | |
| 276 | (CH$_3$)$_2$CH—CH | OC$_2$H$_5$ | H | OCH$_3$ | OCH$_3$ | CH | 98–100 |
| 277 | (CH$_3$)$_2$CH—CH | OC$_2$H$_5$ | CH$_3$ | OCH$_3$ | OCH$_3$ | CH | |
| 278 | (CH$_3$)$_2$CH—CH | OC$_2$H$_5$ | H | OCH$_3$ | Cl | CH | |
| 279 | (CH$_3$)$_2$CH—CH | OC$_2$H$_5$ | H | OCH$_3$ | NHCH$_3$ | CH | |
| 280 | (CH$_3$)$_2$CH—CH | OC$_2$H$_5$ | H | OCH$_3$ | Br | CH | |
| 281 | (CH$_3$)$_2$CH—CH | OC$_2$H$_5$ | H | OCH$_3$ | SCH$_3$ | CH | |
| 282 | (CH$_3$)$_2$CH—CH | OC$_2$H$_5$ | H | OCHF$_2$ | OCH$_3$ | CH | |
| 283 | (CH$_3$)$_2$CH—CH | OC$_2$H$_5$ | H | OCH$_3$ | CH$_3$ | N | |
| 284 | (CH$_3$)$_2$CH—CH | OC$_2$H$_5$ | H | OC$_2$H$_5$ | NHCH$_3$ | N | |
| 285 | (CH$_3$)$_2$CH—CH | OC$_2$H$_5$ | H | OCH$_3$ | N(CH$_3$)$_2$ | N | |
| 286 | cyclopropyl-CH | OCH$_3$ | H | CH$_3$ | CH$_3$ | CH | |
| 287 | cyclopropyl-CH | OCH$_3$ | H | OCH$_3$ | CH$_3$ | CH | |

TABLE 1-continued

| | | | | | | | |
|---|---|---|---|---|---|---|---|
| 288 | —CH | OCH$_3$ | H | OCH$_3$ | OCH$_3$ | CH | |
| 289 | —CH | OCH$_3$ | CH$_3$ | OCH$_3$ | OCH$_3$ | CH | |
| 290 | —CH | OCH$_3$ | H | OCH$_3$ | Cl | CH | |
| 291 | —CH | OCH$_3$ | H | OCH$_3$ | NHCH$_3$ | CH | |
| 292 | —CH | OCH$_3$ | H | OCH$_3$ | Br | CH | |
| 293 | —CH | OCH$_3$ | H | OCH$_3$ | SCH$_3$ | CH | |
| 294 | —CH | OCH$_3$ | H | OCHF$_2$ | OCH$_3$ | CH | |
| 295 | —CH | OCH$_3$ | H | OCH$_3$ | CH$_3$ | N | |
| 296 | —CH | OCH$_3$ | H | OC$_2$H$_5$ | NHCH$_3$ | N | |
| 297 | —CH | OCH$_3$ | H | OCH$_3$ | N(CH$_3$)$_2$ | N | |
| 298 | 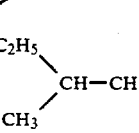 | OC$_2$H$_5$ | H | CH$_3$ | CH$_3$ | CH | |
| 299 | 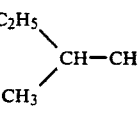 | OC$_2$H$_5$ | H | OCH$_3$ | CH$_3$ | CH | |
| 300 | 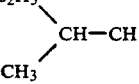 | OC$_2$H$_5$ | H | OCH$_3$ | OCH$_3$ | CH | Resin |
| 301 | 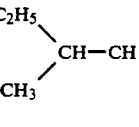 | OC$_2$H$_5$ | CH$_3$ | OCH$_3$ | OCH$_3$ | CH | |
| 302 | 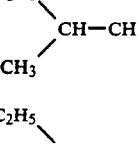 | OC$_2$H$_5$ | H | OCH$_3$ | Cl | CH | |
| 303 | 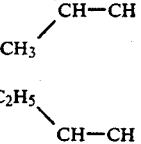 | OC$_2$H$_5$ | H | OCH$_3$ | NHCH$_3$ | CH | |
| 304 |  | OC$_2$H$_5$ | H | OCH$_3$ | Br | CH | |

TABLE 1-continued

| | | | | | | |
|---|---|---|---|---|---|---|
| 305 | C₂H₅\CH—CH/CH₃ | OC₂H₅ | H | OCH₃ | SCH₃ | CH |
| 306 | C₂H₅\CH—CH/CH₃ | OC₂H₅ | H | OCHF₂ | OCH₃ | CH |
| 307 | C₂H₅\CH—CH/CH₃ | OC₂H₅ | H | OCH₃ | CH₃ | N |
| 308 | C₂H₅\CH—CH/CH₃ | OC₂H₅ | H | OC₂H₅ | NHCH₃ | N |
| 309 | C₂H₅\CH—CH/CH₃ | OC₂H₅ | H | OCH₃ | N(CH₃)₂ | N |
| 310 | CH₃\CHCH₂CH/CH₃ | OC₂H₅ | H | CH₃ | CH₃ | CH |
| 311 | CH₃\CHCH₂CH/CH₃ | OC₂H₅ | H | OCH₃ | CH₃ | CH |
| 312 | CH₃\CHCH₂CH/CH₃ | OC₂H₅ | H | OCH₃ | OCH₃ | CH |
| 313 | CH₃\CHCH₂CH/CH₃ | OC₂H₅ | CH₃ | OCH₃ | OCH₃ | CH |
| 314 | CH₃\CHCH₂CH/CH₃ | OC₂H₅ | H | OCH₃ | Cl | CH |
| 315 | CH₃\CHCH₂CH/CH₃ | OC₂H₅ | H | OCH₃ | NHCH₃ | CH |
| 316 | CH₃\CHCH₂CH/CH₃ | OC₂H₅ | H | OCH₃ | Br | CH |
| 317 | CH₃\CHCH₂CH/CH₃ | OC₂H₅ | H | OCH₃ | SCH₃ | CH |
| 318 | CH₃\CHCH₂CH/CH₃ | OC₂H₅ | H | OCHF₂ | OCH₃ | CH |

TABLE 1-continued

| | | | | | | | |
|---|---|---|---|---|---|---|---|
| 319 | (CH$_3$)$_2$CHCH$_2$CH | OC$_2$H$_5$ | H | OCH$_3$ | CH$_3$ | N | |
| 320 | (CH$_3$)$_2$CHCH$_2$CH | OC$_2$H$_5$ | H | OC$_2$H$_5$ | NHCH$_3$ | N | |
| 321 | (CH$_3$)$_2$CHCH$_2$CH | OC$_2$H$_5$ | H | OCH$_3$ | N(CH$_3$)$_2$ | N | |
| 322 | CH$_2$=CH—CH | OC$_2$H$_5$ | H | CH$_3$ | CH$_3$ | CH | |
| 323 | CH$_2$=CH—CH | OC$_2$H$_5$ | H | OCH$_3$ | CH$_3$ | CH | |
| 324 | CH$_2$=CH—CH | OC$_2$H$_5$ | H | OCH$_3$ | OCH$_3$ | CH | |
| 325 | CH$_2$=CH—CH | OC$_2$H$_5$ | CH$_3$ | OCH$_3$ | OCH$_3$ | CH | |
| 326 | CH$_2$=CH—CH | OC$_2$H$_5$ | H | OCH$_3$ | Cl | CH | |
| 327 | CH$_2$=CH—CH | OC$_2$H$_5$ | H | OCH$_3$ | NHCH$_3$ | CH | |
| 328 | CH$_2$=CH—CH | OC$_2$H$_5$ | H | OCH$_3$ | Br | CH | |
| 329 | CH$_2$=CH—CH | OC$_2$H$_5$ | H | OCH$_3$ | SCH$_3$ | CH | |
| 330 | CH$_2$=CH—CH | OC$_2$H$_5$ | H | OCHF$_2$ | OCH$_3$ | CH | |
| 331 | CH$_2$=CH—CH | OC$_2$H$_5$ | H | OCH$_3$ | CH$_3$ | N | |
| 332 | CH$_2$=CH—CH | OC$_2$H$_5$ | H | OC$_2$H$_5$ | NHCH$_3$ | N | |
| 333 | CH$_2$=CH—CH | OC$_2$H$_5$ | H | OCH$_3$ | N(CH$_3$)$_2$ | N | |
| 334 | H$_2$C=CH—C(H)—CH$_2$ | OC$_2$H$_5$ | H | CH$_3$ | CH$_3$ | CH | |
| 335 | H$_2$C=CH—C(H)—CH$_2$ | OC$_2$H$_5$ | H | OCH$_3$ | CH$_3$ | CH | |
| 336 | H$_2$C=CH—C(H)—CH$_2$ | OC$_2$H$_5$ | H | OCH$_3$ | OCH$_3$ | CH | 128–129 |
| 337 | H$_2$C=CH—C(H)—CH$_2$ | OC$_2$H$_5$ | CH$_3$ | OCH$_3$ | OCH$_3$ | CH | |
| 338 | H$_2$C=CH—C(H)—CH$_2$ | OC$_2$H$_5$ | H | OCH$_3$ | Cl | CH | |
| 339 | H$_2$C=CH—C(H)—CH$_2$ | OC$_2$H$_5$ | H | OCH$_3$ | NHCH$_3$ | CH | |
| 340 | H$_2$C=CH—C(H)—CH$_2$ | OC$_2$H$_5$ | H | OCH$_3$ | Br | CH | |
| 341 | H$_2$C=CH—C(H)—CH$_2$ | OC$_2$H$_5$ | H | OCH$_3$ | SCH$_3$ | CH | |
| 342 | H$_2$C=CH—C(H)—CH$_2$ | OC$_2$H$_5$ | H | OCHF$_2$ | OCH$_3$ | CH | |

TABLE 1-continued

| | | | | | | | |
|---|---|---|---|---|---|---|---|
| 343 | H₂C=CH–CH(H)–CH₂– | OC₂H₅ | H | OCH₃ | CH₃ | N | |
| 344 | H₂C=CH–CH(H)–CH₂– | OC₂H₅ | H | OC₂H₅ | NHCH₃ | N | |
| 345 | H₂C=CH–CH(H)–CH₂– | OC₂H₅ | H | OCH₃ | N(CH₃)₂ | N | |
| 346 | ClCH₂—CH | OC₂H₅ | H | CH₃ | CH₃ | CH | |
| 347 | ClCH₂—CH | OC₂H₅ | H | OCH₃ | CH₃ | CH | |
| 348 | ClCH₂—CH | OC₂H₅ | H | OCH₃ | OCH₃ | CH | 68–70 |
| 349 | ClCH₂—CH | OC₂H₅ | CH₃ | OCH₃ | OCH₃ | CH | |
| 350 | CF₃—CH | OC₂H₅ | H | OCH₃ | Cl | CH | |
| 351 | CF₃—CH | OC₂H₅ | H | OCH₃ | NHCH₃ | CH | |
| 352 | CF₃—CH | OC₂H₅ | H | OCH₃ | Br | CH | |
| 353 | CF₃—CH | OC₂H₅ | H | OCH₃ | SCH₃ | CH | |
| 354 | CF₃CF₂—CH | OC₂H₅ | H | OCHF₂ | OCH₃ | CH | |
| 355 | CF₃CF₂—CH | OC₂H₅ | H | OCH₃ | CH₃ | N | |
| 356 | CF₃CF₂—CH | OC₂H₅ | H | OC₂H₅ | NHCH₃ | N | |
| 357 | CF₃CF₂—CH | OC₂H₅ | H | OCH₃ | N(CH₃)₂ | N | |
| 358 | CH₃SCH₂—CH | OC₂H₅ | H | CH₃ | CH₃ | CH | |
| 359 | CH₃SCH₂—CH | OC₂H₅ | H | OCH₃ | CH₃ | CH | |
| 360 | CH₃SCH₂—CH | OC₂H₅ | H | OCH₃ | OCH₃ | CH | |
| 361 | CH₃OCH₂—CH | OC₂H₅ | CH₃ | OCH₃ | OCH₃ | CH | |
| 362 | CH₃OCH₂—CH | OC₂H₅ | H | OCH₃ | Cl | CH | |
| 363 | CH₃OCH₂—CH | OC₂H₅ | H | OCH₃ | NHCH₃ | CH | |
| 364 | CH₃SCH₂CH₂—CH | OC₂H₅ | H | OCH₃ | Br | CH | |
| 365 | CH₃SCH₂CH₂—CH | OC₂H₅ | H | OCH₃ | SCH₃ | CH | |
| 366 | CH₃SCH₂CH₂—CH | OC₂H₅ | H | OCHF₂ | OCH₃ | CH | |
| 367 | CH₃OCH₂CH₂—CH | OC₂H₅ | H | OCH₃ | CH₃ | N | |
| 368 | CH₃OCH₂CH₂—CH | OC₂H₅ | H | OC₂H₅ | NHCH₃ | N | |
| 369 | ClCH₂CH₂CH | OC₂H₅ | H | OCH₃ | N(CH₃)₂ | N | |
| 370 | C₆H₅—CH | OC₂H₅ | H | CH₃ | CH₃ | CH | |
| 371 | C₆H₅—CH | OC₂H₅ | H | OCH₃ | CH₃ | CH | |
| 372 | C₆H₅—CH | OC₂H₅ | H | OCH₃ | OCH₃ | CH | |
| 373 | C₆H₅—CH | OC₂H₅ | CH₃ | OCH₃ | OCH₃ | CH | |
| 374 | C₆H₅—CH | OC₂H₅ | H | OCH₃ | Cl | CH | |
| 375 | 2-Cl-C₆H₄–CH | OC₂H₅ | H | OCH₃ | NHCH₃ | CH | |
| 376 | " | OC₂H₅ | H | OCH₃ | Br | CH | |
| 377 | " | OC₂H₅ | H | OCH₃ | SCH₃ | CH | |
| 378 | 2-Cl-3-OCH₃-C₆H₃–CH | OC₂H₅ | H | OCHF₂ | OCH₃ | CH | |
| 379 | 2,6-F₂-C₆H₃–CH | OCH₃ | H | OCH₃ | CH₃ | N | |

TABLE 1-continued

| | | | | | | | |
|---|---|---|---|---|---|---|---|
| 380 | 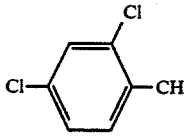 2,4-Cl₂-C₆H₃-CH | OCH₃ | H | OC₂H₅ | NHCH₃ | N | |
| 381 | " | OCH₃ | H | OCH₃ | N(CH₃)₂ | N | |
| 382 | C₆H₅—CH₂—CH | OC₂H₅ | H | CH₃ | CH₃ | CH | |
| 383 | C₆H₅—CH₂—CH | OC₂H₅ | H | OCH₃ | CH₃ | CH | |
| 384 | C₆H₅—CH₂—CH | OC₂H₅ | H | OCH₃ | OCH₃ | CH | 144–145 |
| 385 | C₆H₅—CH₂—CH | OC₂H₅ | CH₃ | OCH₃ | OCH₃ | CH | |
| 386 | C₆H₅—CH₂—CH | OC₂H₅ | H | OCH₃ | Cl | CH | |
| 387 | C₆H₅—CH₂—CH | OC₂H₅ | H | OCH₃ | NHCH₃ | CH | |
| 388 | C₆H₅—CH₂—CH | OC₂H₅ | H | OCH₃ | Br | CH | |
| 389 | C₆H₅—CH₂—CH | OC₂H₅ | H | OCH₃ | SCH₃ | CH | |
| 390 | C₆H₅—CH₂—CH | OC₂H₅ | H | OCHF₂ | OCH₃ | CH | |
| 391 | C₆H₅—CH₂—CH | OC₂H₅ | H | OCH₃ | CH₃ | N | |
| 392 | C₆H₅—CH₂—CH | OC₂H₅ | H | OC₂H₅ | NHCH₃ | N | |
| 393 | C₆H₅—CH₂—CH | OC₂H₅ | H | OCH₃ | N(CH₃)₂ | N | |
| 370 | 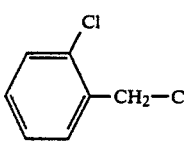 2-Cl-C₆H₄-CH₂-CH | OC₂H₅ | H | CH₃ | CH₃ | CH | |
| 371 | " | OC₂H₅ | H | OCH₃ | CH₃ | CH | |
| 372 | " | OC₂H₅ | H | OCH₃ | OCH₃ | CH | |
| 373 | 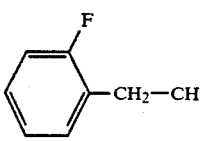 2-F-C₆H₄-CH₂-CH | OC₂H₅ | CH₃ | OCH₃ | OCH₃ | CH | |
| 374 | " | OC₂H₅ | H | OCH₃ | Cl | CH | |
| 375 | " | OC₂H₅ | H | OCH₃ | NHCH₃ | CH | |
| 376 | 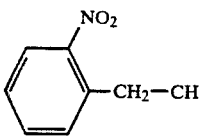 2-NO₂-C₆H₄-CH₂-CH | OC₂H₅ | H | OCH₃ | Br | CH | |
| 377 | " | OC₂H₅ | H | OCH₃ | SCH₃ | CH | |
| 378 | " | OC₂H₅ | H | OCHF₂ | OCH₃ | CH | |
| 379 | 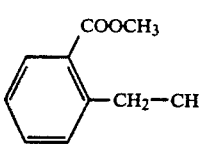 2-COOCH₃-C₆H₄-CH₂-CH | OCH₃ | H | OCH₃ | CH₃ | N | |
| 380 | " | OCH₃ | H | OC₂H₅ | NHCH₃ | N | |
| 381 | " | OCH₃ | H | OCH₃ | N(CH₃)₂ | N | |
| 406 | CH₂=C | OCH₃ | H | CH₃ | CH₃ | CH | |
| 407 | CH₂=C | OCH₃ | H | OCH₃ | CH₃ | CH | |
| 408 | CH₂=C | OCH₃ | H | OCH₃ | OCH₃ | CH | |
| 409 | CH₂=C | OCH₃ | CH₃ | OCH₃ | OCH₃ | CH | |
| 410 | CH₂=C | OCH₃ | H | OCH₃ | Cl | CH | |
| 411 | CH₂=C | OCH₃ | H | OCH₃ | NHCH₃ | CH | |
| 412 | CH₂=C | OCH₃ | H | OCH₃ | Br | CH | |
| 413 | CH₂=C | OCH₃ | H | OCH₃ | SCH₃ | CH | |
| 414 | CH₂=C | OCH₃ | H | OCHF₂ | OCH₃ | CH | |
| 415 | CH₂=C | OCH₃ | H | OCH₃ | CH₃ | N | |
| 416 | CH₂=C | OCH₃ | H | OC₂H₅ | NHCH₃ | N | |
| 417 | CH₂=C | OCH₃ | H | OCH₃ | N(CH₃)₂ | N | |
| 418 | CH₃CH=C | OC₂H₅ | H | CH₃ | CH₃ | CH | |
| 419 | CH₃CH=C | OC₂H₅ | H | OCH₃ | CH₃ | CH | |
| 420 | CH₃CH=C | OC₂H₅ | H | OCH₃ | OCH₃ | CH | 122–123 |
| 421 | CH₃CH=C | OC₂H₅ | CH₃ | OCH₃ | OCH₃ | CH | |
| 422 | CH₃CH=C | OC₂H₅ | H | OCH₃ | Cl | CH | |
| 423 | CH₃CH=C | OC₂H₅ | H | OCH₃ | NHCH₃ | CH | |
| 424 | CH₃CH=C | OC₂H₅ | H | OCH₃ | Br | CH | |
| 425 | CH₃CH=C | OC₂H₅ | H | OCH₃ | SCH₃ | CH | |
| 426 | CH₃CH=C | OC₂H₅ | H | OCHF₂ | OCH₃ | CH | |

TABLE 1-continued

| No. | | | | | | | |
|---|---|---|---|---|---|---|---|
| 427 | CH₃CH=C | OC₂H₅ | H | OCH₃ | CH₃ | N | |
| 428 | CH₃CH=C | OC₂H₅ | H | OC₂H₅ | NHCH₃ | N | |
| 429 | CH₃CH=C | OC₂H₅ | H | OCH₃ | N(CH₃)₂ | N | |
| 430 | C₂H₅CH=C | OC₂H₅ | H | CH₃ | CH₃ | CH | |
| 431 | C₂H₅CH=C | OC₂H₅ | H | OCH₃ | CH₃ | CH | |
| 432 | C₂H₅CH=C | OC₂H₅ | H | OCH₃ | OCH₃ | CH | |
| 433 | C₂H₅CH=C | OC₂H₅ | CH₃ | OCH₃ | OCH₃ | CH | |
| 434 | C₂H₅CH=C | OC₂H₅ | H | OCH₃ | Cl | CH | |
| 435 | C₂H₅CH=C | OC₂H₅ | H | OCH₃ | NHCH₃ | CH | |
| 436 | C₂H₅CH=C | OC₂H₅ | H | OCH₃ | Br | CH | |
| 437 | C₂H₅CH=C | OC₂H₅ | H | OCH₃ | SCH₃ | CH | |
| 438 | C₂H₅CH=C | OC₂H₅ | H | OCHF₂ | OCH₃ | CH | |
| 439 | C₂H₅CH=C | OC₂H₅ | H | OCH₃ | CH₃ | N | |
| 440 | C₂H₅CH=C | OC₂H₅ | H | OC₂H₅ | NHCH₃ | N | |
| 441 | C₂H₅CH=C | OC₂H₅ | H | OCH₃ | N(CH₃)₂ | N | |
| 442 | (CH₃)₂CHCH=C | OC₂H₅ | H | CH₃ | CH₃ | CH | |
| 443 | (CH₃)₂CHCH=C | OC₂H₅ | H | OCH₃ | CH₃ | CH | |
| 444 | (CH₃)₂CHCH=C | OC₂H₅ | H | OCH₃ | OCH₃ | CH | Resin |
| 445 | (CH₃)₂CHCH=C | OC₂H₅ | CH₃ | OCH₃ | OCH₃ | CH | |
| 446 | (CH₃)₂CHCH=C | OC₂H₅ | H | OCH₃ | Cl | CH | |
| 447 | (CH₃)₂CHCH=C | OC₂H₅ | H | OCH₃ | NHCH₃ | CH | |
| 448 | (CH₃)₂CHCH=C | OC₂H₅ | H | OCH₃ | Br | CH | |
| 449 | (CH₃)₂CHCH=C | OC₂H₅ | H | OCH₃ | SCH₃ | CH | |
| 450 | (CH₃)₂CHCH=C | OC₂H₅ | H | OCHF₂ | OCH₃ | CH | |
| 451 | (CH₃)₂CHCH=C | OC₂H₅ | H | OCH₃ | CH₃ | N | |
| 452 | (CH₃)₂CHCH=C | OC₂H₅ | H | OC₂H₅ | NHCH₃ | N | |

TABLE 1-continued

| | | | | | | |
|---|---|---|---|---|---|---|
| 453 | (CH₃)₂CHCH=C | OC₂H₅ | H | OCH₃ | N(CH₃)₂ | N |
| 454 | (CH₃)₂C=C | OC₂H₅ | H | CH₃ | CH₃ | CH |
| 455 | (CH₃)₂C=C | OC₂H₅ | H | OCH₃ | CH₃ | CH |
| 456 | (CH₃)₂C=C | OC₂H₅ | H | OCH₃ | OCH₃ | CH |
| 457 | (CH₃)₂C=C | OC₂H₅ | CH₃ | OCH₃ | OCH₃ | CH |
| 458 | (CH₃)₂C=C | OC₂H₅ | H | OCH₃ | Cl | CH |
| 459 | (CH₃)₂C=C | OC₂H₅ | H | OCH₃ | NHCH₃ | CH |
| 460 | (CH₃)₂C=C | OC₂H₅ | H | OCH₃ | Br | CH |
| 461 | (CH₃)₂C=C | OC₂H₅ | H | OCH₃ | SCH₃ | CH |
| 462 | (CH₃)₂C=C | OC₂H₅ | H | OCHF₂ | OCH₃ | CH |
| 463 | (CH₃)₂C=C | OC₂H₅ | H | OCH₃ | CH₃ | N |
| 464 | (CH₃)₂C=C | OC₂H₅ | H | OC₂H₅ | NHCH₃ | N |
| 465 | (CH₃)₂C=C | OC₂H₅ | H | OCH₃ | N(CH₃)₂ | N |
| 466 | CH₃C(Cl)=C | OC₂H₅ | H | CH₃ | CH₃ | CH |
| 467 | CH₃C(Cl)=C | OC₂H₅ | H | OCH₃ | CH₃ | CH |

TABLE 1-continued

| | | | | | | | |
|---|---|---|---|---|---|---|---|
| 468 | CH₃C(Cl)=C | OC₂H₅ | H | OCH₃ | OCH₃ | CH | |
| 469 | CH₃—C(Br)=C | OC₂H₅ | CH₃ | OCH₃ | OCH₃ | CH | |
| 470 | CH₃—C(Br)=C | OC₂H₅ | H | OCH₃ | Cl | CH | |
| 471 | CH₃—C(Br)=C | OC₂H₅ | H | OCH₃ | NHCH₃ | CH | |
| 472 | CF₃—CH=C | OC₂H₅ | H | OCH₃ | Br | CH | |
| 473 | CCl₃—CH=C | OC₂H₅ | H | OCH₃ | SCH₃ | CH | |
| 474 | CCl₃—CH=C | OC₂H₅ | H | OCHF₂ | OCH₃ | CH | |
| 475 | CCl₃—CH=C | OC₂H₅ | H | OCH₃ | CH₃ | N | |
| 476 | (CF₃)(CF₃)C=C | OC₂H₅ | H | OC₂H₅ | NHCH₃ | N | |
| 477 | (CF₃)(CF₃)C=C | OC₂H₅ | H | OCH₃ | N(CH₃)₂ | N | |
| 478 | C₆H₅—CH=C | OC₂H₅ | H | CH₃ | CH₃ | CH | |
| 479 | C₆H₅—CH=C | OC₂H₅ | H | OCH₃ | CH₃ | CH | |
| 480 | C₆H₅—CH=C | OC₂H₅ | H | OCH₃ | OCH₃ | CH | |
| 481 | C₆H₅—CH=C | OC₂H₅ | CH₃ | OCH₃ | OCH₃ | CH | |
| 482 | C₆H₅—CH=C | OC₂H₅ | H | OCH₃ | Cl | CH | |
| 483 | C₆H₅—CH=C | OC₂H₅ | H | OCH₃ | NHCH₃ | CH | |
| 484 | C₆H₅—CH=C | OC₂H₅ | H | OCH₃ | Br | CH | |
| 485 | C₆H₅—CH=C | OC₂H₅ | H | OCH₃ | SCH₃ | CH | |
| 486 | C₆H₅—CH=C | OC₂H₅ | H | OCHF₂ | OCH₃ | CH | |
| 487 | C₆H₅—CH=C | OC₂H₅ | H | OCH₃ | CH₃ | N | |
| 488 | C₆H₅—CH=C | OC₂H₅ | H | OC₂H₅ | NHCH₃ | N | |
| 489 | C₆H₅—CH=C | OC₂H₅ | H | OCH₃ | N(CH₃)₂ | N | |
| 490 | CH₃—CH | N(CH₃)₂ | H | CH₃ | CH₃ | CH | |
| 491 | CH₃—CH | N(CH₃)₂ | H | OCH₃ | CH₃ | CH | |
| 492 | CH₃—CH | N(CH₃)₂ | H | OCH₃ | OCH₃ | CH | |
| 493 | CH₃—CH | N(CH₃)₂ | CH₃ | OCH₃ | OCH₃ | CH | |
| 494 | CH₃—CH | N(CH₃)₂ | H | OCH₃ | Cl | CH | |
| 495 | CH₃—CH | N(CH₃)₂ | H | OCH₃ | NHCH₃ | CH | |
| 496 | CH₃—CH | N(CH₃)₂ | H | OCH₃ | Br | CH | |
| 497 | CH₃—CH | N(CH₃)₂ | H | OCH₃ | SCH₃ | CH | |
| 498 | CH₃—CH | N(CH₃)₂ | H | OCHF₂ | OCH₃ | CH | |
| 499 | CH₃—CH | N(CH₃)₂ | H | OCH₃ | CH₃ | N | |
| 500 | CH₃—CH | N(CH₃)₂ | H | OC₂H₅ | NHCH₃ | N | |
| 501 | CH₃—CH | N(CH₃)₂ | H | OCH₃ | N(CH₃)₂ | N | |
| 502 | C₂H₅—CH | N(CH₃)₂ | CH₃ | OCH₃ | OCH₃ | CH | |
| 503 | C₂H₅—CH | N(CH₃)₂ | H | OCH₃ | OCH₃ | CH | 184–186 |
| 504 | C₂H₅—CH | N(CH₃)₂ | H | OCH₃ | Cl | CH | |
| 505 | C₂H₅—CH | N(CH₃)₂ | H | OCH₃ | CH₃ | N | |
| 506 | C₃H₇—CH | N(CH₃)₂ | H | OCH₃ | OCH₃ | CH | |
| 507 | C₃H₇—CH | N(CH₃)₂ | H | OCH₃ | CH₃ | N | |
| 508 | C₃H₇—CH | N(CH₃)₂ | H | OCH₃ | Cl | CH | |
| 509 | C₃H₇—CH | N(CH₃)₂ | H | OCH₃ | OCH₃ | CH | |
| 510 | C₃H₇—CH | N(CH₃)₂ | H | OCH₃ | CH₃ | N | |
| 511 | CH₃CH=C | N(CH₃)₂ | CH₃ | OCH₃ | OCH₃ | CH | |
| 512 | CH₃CH=C | N(CH₃)₂ | H | OCH₃ | OCH₃ | CH | |
| 513 | CH₃CH=C | N(CH₃)₂ | H | OCH₃ | Cl | CH | |
| 514 | CH₃CH₂CH=C | N(CH₃)₂ | H | OCH₃ | CH₃ | N | |
| 515 | C₆H₅—CH=C | N(CH₃)₂ | H | OCH₃ | OCH₃ | CH | 142 |
| 516 | " | N(CH₃)₂ | H | OCH₃ | CH₃ | N | |
| 517 | " | N(CH₃)₂ | H | OCH₃ | Cl | CH | |
| 518 | " | N(CH₃)₂ | H | OCH₃ | OCH₃ | CH | |
| 519 | " | N(CH₃)OCH₃ | H | OCH₃ | CH₃ | N | |

TABLE 1-continued

| | | | | | | | |
|---|---|---|---|---|---|---|---|
| 520 | (CH₃)(CH₃)C=C | N(CH₃)₂ | CH₃ | OCH₃ | OCH₃ | CH | |
| 521 | (CH₃)(CH₃)C=C | N(CH₃)₂ | H | OCH₃ | OCH₃ | CH | |
| 522 | (CH₃)(CH₃)C=C | N(CH₃)₂ | H | OCH₃ | Cl | CH | |
| 523 | (CH₃)(CH₃)C=C | N(CH₃)₂ | H | OCH₃ | CH₃ | N | |
| 524 | (CH₃)(CH₃)C=C | N(CH₃)₂ | H | OCH₃ | OCH₃ | CH | |
| 525 | (CH₃)(CH₃)C=C | N(CH₃)₂ | H | OCH₃ | CH₃ | N | |
| 526 | (CH₃)(CH₃)C=C | N(CH₃)₂ | H | OCH₃ | Cl | CH | |
| 527 | (CH₃)(CH₃)C=C | N(CH₃)₂ | H | OCH₃ | OCH₃ | CH | |
| 528 | (CH₃)(CH₃)C=C | N(CH₃)₂ | H | OCH₃ | CH₃ | N | |
| 529 | C₂H₅—CH | NHCH₃ | CH₃ | OCH₃ | OCH₃ | CH | |
| 530 | C₂H₅—CH | SC₂H₅ | H | OCH₃ | OCH₃ | CH | |
| 531 | (CH₃)₂C | OC₂H₅ | H | OCH₃ | Cl | CH | |
| 532 | C₂H₅(CH₃)C | OC₂H₅ | H | OCH₃ | CH₃ | N | |
| 533 | C₆H₅—CH₂(CH₃)C | OC₂H₅ | H | OCH₃ | OCH₃ | CH | |
| 534 | cyclopropyl | OC₂H₅ | H | OCH₃ | CH₃ | N | 145–146 |
| 535 | cyclohexyl (gem-dimethyl) | OC₂H₅ | H | OCH₃ | Cl | CH | |
| 536 | CH₂=CHCH₂(CH₂)C | OC₂H₅ | H | OCH₃ | OCH₃ | CH | |
| 537 | CH₂=CHCH₂(CH₂)C | OC₂H₅ | H | OCH₃ | CH₃ | N | |

(L) denotes: L isomer
(D) denotes: D isomer

TABLE 2

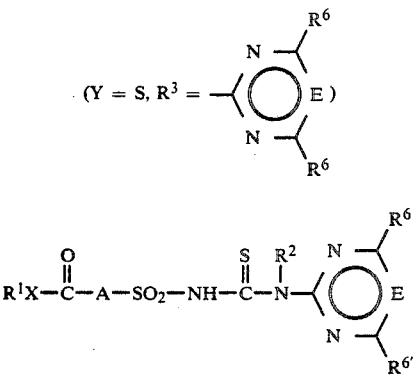

| Example No. | A | XR¹ | R² | R⁶ | R⁶' | E | M.p. °C. |
|---|---|---|---|---|---|---|---|
| 538 | $C_2H_5$—CH | $OCH_3$ | H | $OCH_3$ | $OCH_3$ | CH | |
| 539 | $C_2H_5$—CH | $OCH_3$ | $CH_3$ | $OCH_3$ | $OCH_3$ | CH | |
| 540 | $C_2H_5$—CH | $OC_2H_5$ | H | $OCH_3$ | $OCH_3$ | CH | |
| 541 | $C_6H_5$—CH=C | $OC_2H_5$ | H | $OCH_3$ | $CH_3$ | N | |
| 542 | $C_2H_5$—CH | $N(CH_3)_2$ | H | $OCH_3$ | $OCH_3$ | CH | |
| 543 | $C_6H_5$—$CH_2CH$ | $OCH_3$ | H | $OCH_3$ | $CH_3$ | N | |
| 544 | $CH_2$=$CHCH_2$—CH | $OCH_3$ | H | $OCH_3$ | $OCH_3$ | CH | |
| 545 | CH≡C—$CH_2CH$ | $OCH_3$ | H | $OCH_3$ | Cl | CH | |
| 546 | $CCl_3CH$=C | $OCH_3$ | H | $OCH_3$ | $OCH_3$ | CH | |

TABLE 3

(Y = O, R² = H)

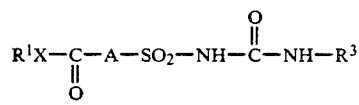

| Example No. | A | XR¹ | R³ | M.p. °C. |
|---|---|---|---|---|
| 547 | $CH_2$ | $OCH_3$ | -CH₂-(2,6-dimethoxypyrimidin-4-yl) | |
| 548 | $CH_2$ | $OC_2H_5$ | " | |
| 549 | $CH_3$—CH | $OCH_3$ | " | |
| 550 | $C_2H_5$—CH | $OC_2H_5$ | " | |
| 551 | $C_3H_7$—CH | $OCH_3$ | " | |
| 552 | $C_3H_7$—CH | $OC_2H_5$ | " | |
| 553 | $CH_2$ | $OCH_3$ | -CH₂-(2,6-dimethoxypyrazin) | |
| 554 | $CH_2$ | $OC_2H_5$ | " | |
| 555 | $CH_3$—CH | $OCH_3$ | " | |
| 556 | $C_2H_5$—CH | $OC_2H_5$ | " | |
| 557 | $CH_2$ | $OCH_3$ | -CH₂-(4,6-dimethylpyrimidin-2-yl) | |
| 558 | $CH_2$ | $OC_2H_5$ | " | |

TABLE 3-continued (Y = O, R² = H)

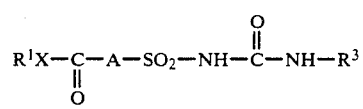

| Example No. | A | XR¹ | R³ | M.p. °C. |
|---|---|---|---|---|
| 559 | $CH_3$—CH | $OC_2H_5$ | " | |
| 560 | $C_2H_5$—CH | $OC_2H_5$ | " | |
| 561 | $C_3H_7$—CH | $OC_2H_5$ | " | |
| 562 | $CH_2$ | $OCH_3$ | 2,4-dimethyl-cyclopenta[b]pyridine | |
| 563 | $CH_3$—CH | $OCH_3$ | " | |
| 564 | $CH_3$—CH | $OC_2H_5$ | " | |
| 565 | $C_2H_5$—CH | $OC_2H_5$ | " | |
| 566 | $C_3H_7$—CH | $OC_2H_5$ | " | |
| 567 | $CH_2$ | $OC_2H_5$ | 2-methyl-4-methoxy-cyclopenta[b]pyridine | |
| 568 | $CH_3$—CH | $OC_2H_5$ | " | |
| 569 | $C_2H_5$—CH | $OC_2H_5$ | " | |
| 570 | $C_3H_7$—CH | $OC_2H_5$ | " | |
| 571 | $CH_2$ | $OC_2H_5$ | 1,3,5-trimethylpyrazole | |

TABLE 3-continued (Y = O, R² = H)

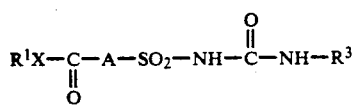

$$R^1X-\underset{\underset{O}{\|}}{\overset{\overset{O}{\|}}{C}}-A-SO_2-NH-\overset{\overset{O}{\|}}{C}-NH-R^3$$

| Example No. | A | XR¹ | R³ | M.p. °C. |
|---|---|---|---|---|
| 572 | CH₃—CH | OC₂H₅ | " | |
| 573 | C₂H₅—CH | OC₂H₅ | " | |
| 574 | C₃H₇—CH | OC₂H₅ | " | |
| 575 | CH₂ | OC₂H₅ | (pyrazole-triazine with CH₃, OCH₃) | |
| 576 | CH₃—CH | OC₂H₅ | " | |
| 577 | C₂H₅—CH | OC₂H₅ | " | |
| 578 | C₃H₇—CH | OC₂H₅ | " | |
| 579 | CH₂ | OC₂H₅ | (fused bicyclic, OH) | |
| 580 | CH₃—CH | OC₂H₅ | " | |
| 581 | C₂H₅—CH | OC₂H₅ | " | |
| 582 | C₃H₇—CH | OC₂H₅ | " | |
| 583 | CH₂ | OC₂H₅ | (fused bicyclic, CH₃) | |
| 584 | CH₃—CH | OC₂H₅ | " | |
| 585 | C₂H₃—CH | OC₂H₅ | " | |
| 586 | C₃H₇—CH | OC₂H₅ | " | |
| 587 | CH₂ | OC₂H₅ | (fused bicyclic, CH₃, CH₃) | |
| 588 | CH₃—CH | OC₂H₅ | " | |
| 589 | C₂H₅—CH | OC₂H₅ | " | |
| 590 | C₃H₇—CH | OC₂H₅ | " | |
| 591 | CH₂ | OC₂H₅ | (fused bicyclic, CH₃, OCH₃) | |
| 592 | CH₃—CH | OC₂H₅ | " | |
| 593 | C₂H₅—CH | OC₂H₅ | " | |
| 594 | C₃H₇—CH | OC₂H₅ | " | |

Biological Examples

The damage to the weed plants and the tolerance by crop plants were scored using a key in which the effectiveness is expressed in figures from 0 to 5. In this key, the figures denote:

0 = without action
1 = 0 to 20% action or damage
2 = 20 to 40% action or damage
3 = 40 to 60% action or damage
4 = 60 to 80% action or damage
5 = 80 to 100% action or damage 1. Action against weeds in the pre-emergence method Seeds or rhizome pieces of monocotyledon and dicotyledon weed plants were placed in sandy loam soil in plastic pots and covered with soil. The compounds according to the invention which were formulated in the form of wettable powders or emulsion concentrates were then applied as aqueous suspensions or emulsions at an application rate of 600 to 800 l of water/ha (converted) to the surface of the cover soil at various dosages.

After the treatment, the pots were placed in the greenhouse and maintained under good growth conditions for the weeds. Visual scoring of the damage to the plants, or the emergence damage, was carried out after the test plants had emerged, after a test period of 3 to 4 weeks in the form of a comparison with untreated controls. As shown by the scoring data in Table 1, the compounds according to the invention show a good herbicidal preemergence effectiveness against a broad range of weed grasses and weeds.

2. Action against weeds in the post-emergence method

Seeds or rhizome pieces of monocotyledon and dicotyledon weeds were placed in sandy loam soil in plastic pots, covered with soil and grown in the greenhouse under good growth conditions. Three weeks after sowing, the test plants were treated in the three-leaf stage.

The compounds according to the invention, which were formulated as wettable powders or emulsion concentrates, were sprayed in various dosages to the green parts of the plants at an application rate of 600 to 800 l of water/ha (converted), and the action of the preparations was scored visually after the test plants had remained in the greenhouse under optimum growth conditions for approx. 3 to 4 weeks, in the form of a comparison with untreated controls.

The agents according to the invention also show a good herbicidal effectiveness against a broad range of economically important weed grasses and weeds when applied using the post-emergence method (Table II).

3. Tolerance by crop plants

In further greenhouse experiments, seeds of a fairly large number of crop plants and weeds were placed in sandy loam soil and covered with soil.

Some of the pots were treated immediately as described under 1., the remaining ones were placed in the greenhouse until the plants had developed 2 to 3 true leaves and were then sprayed as described under 2. with the substances according to the invention in various dosages.

4 to 5 weeks after the application and after standing in the greenhouse, it was found by means of visual scoring that the compounds according to the invention did not cause any damage on dicotyledon crops, for example soya beans, cotton, oil seed rape, sugar beet and potatoes, when used in the pre- and post-emergence methods, even when high doses of active substance were used. Moreover, some substances even left Gramineae crops, for example barley, wheat, rye, Sorghum millets, maize or rice, undamaged. The compounds of the formula I therefore show a high selectivity when used for controlling undesired plant growth in agricultural crops.

TABLE 1

Pre-emergence action of the compounds according to the invention

| No. | Product Dosage kg of a.i./ha | Herbicidal action | | | |
|---|---|---|---|---|---|
| | | SIA | CRS | STM | LOM |
| 1 | 0.6 | 5 | 5 | 5 | 5 |
| 2 | 0.6 | 5 | 5 | 5 | 5 |
| 3 | 0.6 | 5 | 5 | 2 | 5 |
| 4 | 0.6 | 5 | 5 | 5 | 5 |
| 6 | 0.6 | 5 | 5 | 5 | 5 |
| 16 | 0.6 | 5 | 3 | 5 | 4 |
| 28 | 0.6 | 5 | 5 | 5 | 5 |
| 32 | 0.6 | 5 | 5 | 5 | 5 |
| 40 | 0.6 | 5 | 5 | 5 | 5 |
| 46 | 0.6 | 5 | 5 | 5 | 4 |
| 49 | 0.6 | 5 | 2 | 5 | 5 |
| 64 | 0.6 | 5 | 5 | 4 | 2 |
| 77 | 0.6 | 5 | 5 | 4 | 3 |
| 82 | 0.6 | 5 | 5 | 5 | 5 |
| 136 | 0.6 | 5 | 5 | 5 | 5 |
| 154 | 0.6 | 5 | 4 | 5 | 5 |
| 157 | 0.6 | 5 | 5 | 4 | 4 |
| 230 | 0.6 | 4 | 5 | 5 | 2 |
| 264 | 0.6 | 5 | 5 | 5 | 3 |
| 276 | 0.6 | 5 | 4 | 3 | 5 |
| 300 | 0.6 | 5 | 5 | 5 | 4 |
| 336 | 0.6 | 5 | 5 | 4 | 2 |
| 384 | 0.6 | 4 | 5 | 4 | 5 |
| 420 | 0.6 | 5 | 5 | 5 | 5 |
| 444 | 0.6 | 5 | 3 | 5 | 4 |
| 503 | 0.6 | 5 | 5 | 5 | 2 |

TABLE II

Post-emergence action

| No. | Product Dosage kg of a.i./ha | Herbicidal action | | | |
|---|---|---|---|---|---|
| | | SIA | CRS | STM | LOM |
| 1 | 0.6 | 5 | 5 | 5 | 5 |
| 2 | 0.6 | 5 | 5 | 5 | 5 |
| 3 | 0.6 | 5 | 5 | 4 | 5 |
| 4 | 0.6 | 5 | 5 | 5 | 5 |
| 6 | 0.6 | 4 | 5 | 5 | 5 |
| 16 | 0.6 | 5 | 5 | 5 | 5 |
| 28 | 0.6 | 5 | 5 | 5 | 5 |
| 32 | 0.6 | 5 | 5 | 5 | 5 |
| 40 | 0.6 | 5 | 5 | 5 | 5 |
| 46 | 0.6 | 5 | 5 | 5 | 5 |
| 49 | 0.6 | 5 | 5 | 5 | 5 |
| 65 | 0.6 | 5 | 5 | 5 | 5 |
| 77 | 0.6 | 5 | 5 | 5 | 5 |
| 82 | 0.6 | 5 | 5 | 5 | 5 |
| 136 | 0.6 | 5 | 5 | 5 | 5 |
| 154 | 0.6 | 5 | 5 | 5 | 4 |
| 157 | 0.6 | 5 | 5 | 5 | 5 |
| 230 | 0.6 | 4 | 5 | 5 | 5 |
| 264 | 0.6 | 5 | 5 | 5 | 5 |
| 276 | 0.6 | 5 | 4 | 5 | 5 |
| 300 | 0.6 | 4 | 5 | 5 | 5 |
| 336 | 0.6 | 5 | 5 | 5 | 4 |
| 384 | 0.6 | 5 | 5 | 5 | 5 |
| 420 | 0.6 | 5 | 5 | 5 | 5 |
| 444 | 0.6 | 5 | 5 | 5 | 5 |
| 503 | 0.6 | 5 | 5 | 5 | 5 |

Abbreviations:
SIA = Sinapis alba
CRS = Chrysanthemum segetum
STM = Stellaria media
LOM = Lolium multiflorum Inhibition of growth in cereals In greenhouse dish experiments, young cereal plants (wheat, barley, rye) were sprayed in the 3-leaf stage with the compounds according to the invention in various active substance concentrations (kg/ha) until dripping wet.

After the untreated control plants had reached a plant height of approximately 55 cm, the additional growth was measured in all plants, and the inhibition of growth of additional growth of the control plants was calculated as a percentage. Moreover, the phytotoxic action of the compounds was observed, in which case 100% denotes that growth has ceased, and 0% denotes growth corresponding to that of the untreated control plants. It emerged that the compounds possess very good growth-regulating properties. The results are compiled in Table III below.

TABLE III

| Compounds of Ex. No. | Application conc. in kg/ha | Inhibition of growth (%) | | | Phytotoxic Action |
|---|---|---|---|---|---|
| | | Wheat | Barley | Rye | |
| 1 | 0.62 | 22 | 32 | 19 | No |
| | 0.31 | 17 | 24 | 17 | damage |
| 16 | 0.62 | 23 | 37 | 24 | No |
| | 0.31 | 17 | 22 | 16 | damage |
| 154 | 0.62 | 21 | 34 | 24 | No |
| | 0.31 | 16 | 21 | 17 | damage |
| 276 | 0.62 | 24 | 26 | 23 | No |
| | 0.31 | 19 | 23 | 18 | damage |

We claim:
1. A compound of formula I

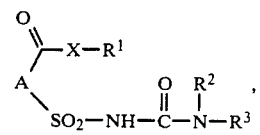

or a stereoisomer thereof, wherein:
A is a radical of formula $>C(R^4)_2$ or $>C=(R^5)_2$;
$R^1$ is H, $(C_1-C_8)$alkyl, $(C_2-C_8)$alkenyl, $(C_2-C_8)$alkynyl, it being possible for these aliphatic radicals to be monosubstituted or polysubstituted by halogen, or to be monosubstituted or disubstituted by $(C_1-C_6)$alkoxy, $(C_2-C_6)$alkenyloxy, $(C_2-C_6)$alkynyloxy, $(C_1-C_6)$alkylthio, $(C_1-C_6)$alkylsulfinyl, $(C_1-C_6)$alkylsulfonyl, $(C_1-C_6)$alkoxycarbonyl or by phenyl; or is $(C_3-C_8)$cycloalkyl which can be monosubstituted or polysubstituted by halogen, or monosubstituted or disubstituted by $(C_1-C_4)$alkoxy or ($C_1-C_4$)alkylthio; or is $(C_5-C_8)$cycloalkenyl, cyclopropylmethyl, epoxypropyl, furfuryl, tetrahydrofurfuryl, or phenoxy$(C_1-C_6)$alkyl or phenyl both of which can be substituted in the phenyl ring by halogen, $(C_1-C_4)$alkyl, $(C_1-C_4)$alkoxy or $NO_2$;
$R^2$ is H, $(C_1-C_8)$alkyl, $(C_2-C_8)$alkenyl, $(C_2-C_8)$alkynyl or $(C_1-C_4)$alkoxy;
$R^3$ is a radical of formula

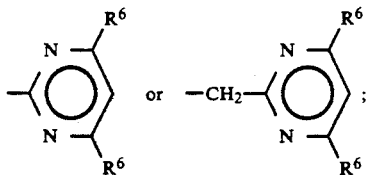

the R⁴ radicals independently of one another are H, (C₁-C₆)alkyl, (C₂-C₆)alkenyl, (C₂-C₆)alkynyl, (C₃-C₈)cycloalkyl, it being possible for the above-mentioned radicals which contain C to be monosubstituted or polysubstituted by halogen or monosubstituted or disubstituted by (C₁-C₆)alkoxy, (C₂-C₆)alkenyloxy, (C₂-C₆)alkynyloxy, (C₁-C₆)alkylthio, (C₁-C₆)alkylsulfinyl, (C₁-C₆)alkylsulfonyl or (C₁-C₆)alkoxycarbonyl, or by phenyl which can be monosubstituted or polysubstituted by halogen, (C₁-C₄)alkyl, (C₁-C₄)alkoxy, (C₁-C₄)alkylthio, (C₁-C₄)alkoxycarbonyl or NO₂, it being furthermore possible for one of the two radicals R⁴ to be phenyl which can be monosubstituted or polysubstituted by halogen, (C₁-C₄)alkyl, (C₁-C₄)alkoxy, NO₂ or CF₃, or for the two radicals R⁴ together to be an alkylene radical —(CH₂)ₘ—;

the R⁵ radicals independently of one another are H, or (C₁-C₆)alkyl which can be monosubstituted or polysubstituted by halogen or monosubstituted or disubstituted by (C₁-C₆)alkoxy, (C₁-C₆)alkylthio, (C₁-C₆)alkylsulfinyl or (C₁-C₆)alkoxycarbonyl, or it being possible for one of the radicals R⁵ to be phenyl which can be monosubstituted or polysubstituted by halogen, (C₁-C₄)alkyl, (C₁-C₄)alkoxy, NO₂, CF₃ or (C₁-C₆)alkoxycarbonyl, or for the two radicals R⁵ together to be an alkylene radical —(CH₂)ₙ—;

the R⁶ radicals independently of one another are H, halogen, or (C₁-C₆)alkyl, (C₁-C₆)alkoxy or (C₁-C₆)alkylthio which can be monosubstituted or polysubstituted by halogen or monosubstituted or disubstituted by (C₁-C₄)alkoxy or (C₁-C₄)alkylthio; or are a radical N(R¹¹)₂, (C₃-C₆)cycloalkyl, —OCHR⁷COOR¹¹, (C₃-C₅)alkenyl, (C₂-C₄)alkynyl, (C₃-C₅)alkenyloxy or (C₃-C₅)alkynyloxy;

R⁷ is H or (C₁-C₄)alkyl;

R⁸ is (C₁-C₄)alkyl, —CHF₂ or —CH₂CF₃;

the R¹¹ radicals independently of one another are H, (C₁-C₄)alkyl, (C₂-C₄)alkenyl or (C₃-C₄)alkynyl;

X is O, S or NR¹²;

Y is O or S;

R¹² is H, (C₁-C₆)alkyl, (C₂-C₆)alkenyl, (C₂-C₆)alkynyl, (C₁-C₆)alkoxy, or a radical of formula

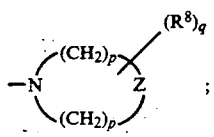

m is an integer from 2 to 6;
n is an integer from 3 to 6;
p is an integer from 1 to 3;
q is an integer from 0 to 3; and
Z is O, S, CH₂, NH or N(C₁-C₄-alkyl), or an agriculturally acceptable salt thereof.

2. A compound of formula I as claimed in claim 1 wherein:

A is a radical >C(R⁴)₂ or >C=C(R⁵)₂;

R¹ is (C₁-C₄)alkyl which can be monosubstituted or polysubstituted by halogen or monosubstituted to disubstituted by (C₁-C₄)alkoxy;

R² is H, (C₁-C₄)alkyl or allyl;

R³ is a radical of formula

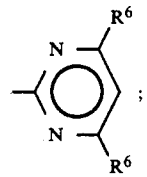

the R⁴ radicals independently of one another are H, or (C₁-C₆)alkyl which can be monosubstituted or polysubstituted by halogen or monosubstituted or disubstituted by (C₁-C₄)alkoxy or (C₁-C₄)alkylthio; or a radical R⁴ is (C₂-C₆)alkenyl or phenyl which can be substituted as indicated above; a radical R⁴ is (C₁-C₄)alkyl or phenyl which is monosubstituted to trisubstituted by fluorine, chlorine, (C₁-C₄)alkoxy, (C₁-C₄)alkyl or nitro, and the other radical R⁴ is hydrogen;

the R⁵ radicals independently of one another are H, or (C₁-C₆)alkyl, which can be monosubstituted or polysubstituted by halogen;

the R⁶ radicals independently of one another are halogen, or are (C₁-C₄)alkyl or (C₁-C₄)alkoxy, both of which can be halogenated;

X is O, S or NR¹²;

Y is O or S; and

R¹² is H, (C₁-C₄)alkyl or (C₂-C₄)alkenyl.

3. A compound as claimed in claim 2, wherein R¹ is (C₁-C₄)alkyl, R² is H and R⁶ is CH₃, OCH₃, OC₂H₅, Cl or OCF₂H.

4. A herbicidal composition comprising 2 to 90% by weight of a compound of formula I

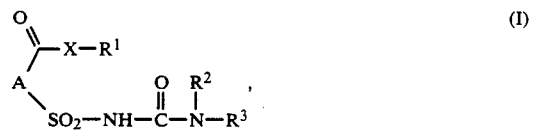

or a stereoisomer thereof, wherein:

A is a radical of formula >C(R⁴)₂ or >C=(R⁵)₂;

R¹ is H, (C₁-C₈)alkyl, (C₂-C₈)alkenyl, (C₂-C₈)alkynyl, it being possible for these aliphatic radicals to be monosubstituted or polysubstituted by halogen, or to be monosubstituted or disubstituted by (C₁-C₆)alkoxy, (C₂-C₆)alkenyloxy, (C₂-C₆)alkynyloxy, (C₁-C₆)alkylthio, (C₁-C₆)alkylsulfinyl, (C₁-C₆)alkylsulfonyl, (C₁-C₆)alkoxycarbonyl or by phenyl; or is (C₃-C₈)cycloalkyl which can be monosubstituted or polysubstituted by halogen, or monosubstituted or disubstituted by (C₁-C₄)alkoxy or (C₁-C₄)alkylthio; or is (C₅-C₈)cycloalkenyl, cyclopropylmethyl, epoxypropyl, furfuryl, tetrahydrofurfuryl, or phenoxy(C₁-C₆)alkyl or phenyl both of which can be substituted in the phenyl ring by halogen, (C₁-C₄)alkyl, (C₁-C₄)alkoxy or NO₂;

R² is H, (C₁-C₈)alkyl, (C₂-C₈)alkenyl, (C₂-C₈)alkynyl or (C₁-C₄)alkoxy;

$R^3$ is a radical of formula

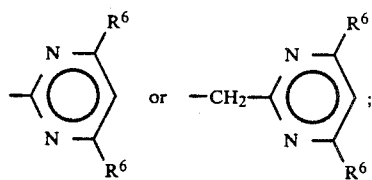

the $R^4$ radicals independently of one another are H, $(C_1-C_6)$alkyl, $(C_2-C_6)$alkenyl, $(C_2-C_6)$alkynyl, $(C_3-C_8)$cycloalkyl, it being possible for the above-mentioned radicals which contain C to be monosubstituted or polysubstituted by halogen or monosubstituted or disubstituted by $(C_1-C_6)$alkoxy, $(C_2-C_6)$alkenyloxy, $(C_2-C_6)$alkynyloxy, $(C_1-C_6)$alkylthio, $(C_1-C_6)$alkylsulfinyl, $(C_1-C_6)$alkylsulfonyl or $(C_1-C_6)$alkoxycarbonyl, or by phenyl which can be monosubstituted or polysubstituted by halogen, $(C_1-C_4)$alkyl, $(C_1-C_4)$alkoxy, $(C_1-C_4)$alkylthio, $(C_1-C_4)$alkoxycarbonyl or $NO_2$, it being furthermore possible for one of the two radicals $R^4$ to be phenyl which can be monosubstituted or polysubstituted by halogen, $(C_1-C_4)$alkyl, $(C_1-C_4)$alkoxy, $NO_2$ or $CF_3$, or for the two radicals $R^4$ together to be an alkylene radical $—(CH_2)_m—$;

the $R^5$ radicals independently of one another are H, or $(C_1-C_6)$alkyl which can be monosubstituted or polysubstituted by halogen or monosubstituted or disubstituted by $(C_1-C_6)$alkoxy, $(C_1-C_6)$alkylthio, $(C_1-C_6)$alkylsulfinyl or $(C_1-C_6)$alkoxycarbonyl, or it being possible for one of the radicals $R^5$ to be phenyl which can be monosubstituted or polysubstituted by halogen, $(C_1-C_4)$alkyl, $(C_1-C_4)$alkoxy, $NO_2$, $CF_3$ or $(C_1-C_6)$alkoxycarbonyl, or for the two radicals $R^5$ together to be an alkylene radical $—(CH_2)_n—$;

the $R^6$ radicals independently of one another are H, halogen, or $(C_1-C_6)$alkyl, $(C_1-C_6)$alkoxy or $(C_1-C_6)$alkylthio which can be monosubstituted or polysubstituted by halogen or monosubstituted or disubstituted by $(C_1-C_4)$alkoxy or $(C_1-C_4)$alkylthio; or are a radical $N(R^{11})_2$, $(C_3-C_6)$cycloalkyl, $—OCHR^7COOR^{11}$, $(C_3-C_5)$alkenyl, $(C_2-C_4)$alkynyl, $(C_3-C_5)$alkenyloxy or $(C_3-C_5)$alkynyloxy;

$R^7$ is H or $(C_1-C_4)$alkyl;

$R^8$ is $(C_1-C_4)$alkyl, $—CHF_2$ or $—CH_2CF_3$;

the $R^{11}$ radicals independently of one another are H, $(C_1-C_4)$alkyl, $(C_2-C_4)$alkenyl or $(C_3-C_4)$alkynyl;

X is O, S or $NR^{12}$;

Y is O or S;

$R^{12}$ is H, $(C_1-C_6)$alkyl, $(C_2-C_6)$alkenyl, $(C_2-C_6)$alkynyl, $(C_1-C_6)$alkoxy, or a radical of formula

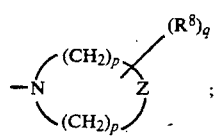

m is an integer from 2 to 6;
n is an integer from 3 to 6;
p is an integer from 1 to 3;
q is an integer from 0 to 3; and Z is O, S, $CH_2$, NH or $N(C_1-C_4$-alkyl), or an agriculturally acceptable salt thereof and the remainder to 100% by weight of an inert auxiliary.

5. A plant-growth regulating composition comprising 2 to 90% by weight of a compound of formula I

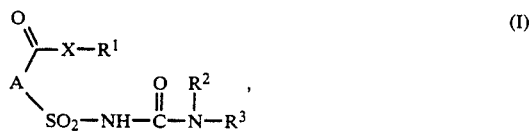

or a stereoisomer thereof, wherein:

A is a radical of formula $>C(R^4)_2$ or $>C=(R^5)_2$;

$R^1$ is H, $(C_1-C_8)$alkyl, $(C_2-C_8)$alkenyl, $(C_2-C_8)$alkynyl, it being possible for these aliphatic radicals to be monosubstituted or polysubstituted by halogen, or to be monosubstituted or disubstituted by $(C_1-C_6)$alkoxy, $(C_2-C_6)$alkenyloxy, $(C_2-C_6)$alkynyloxy, $(C_1-C_6)$alkylthio, $(C_1-C_6)$alkylsulfinyl, $(C_1-C_6)$alkylsulfonyl, $(C_1-C_6)$alkoxycarbonyl or by phenyl; or is $(C_3-C_8)$cycloalkyl which can be monosubstituted or polysubstituted by halogen, or monosubstituted or disubstituted by $(C_1-C_4)$alkoxy or $(C_1-C_4)$alkylthio; or is $(C_5-C_8)$cycloalkenyl, cyclopropylmethyl, epoxypropyl, furfuryl, tetrahydrofurfuryl, or phenoxy$(C_1-C_6)$alkyl or phenyl both of which can be substituted in the phenyl ring by halogen, $(C_1-C_4)$alkyl, $(C_1-C_4)$alkoxy or $NO_2$;

$R^2$ is H, $(C_1-C_8)$alkyl, $(C_2-C_8)$alkenyl, $(C_2-C_8)$alkynyl or $(C_1-C_4)$alkoxy;

$R^3$ is a radical of formula

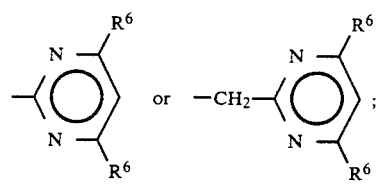

the $R^4$ radicals independently of one another are H, $(C_1-C_6)$alkyl, $(C_2-C_6)$alkenyl, $(C_2-C_6)$alkynyl, $(C_3-C_8)$cycloalkyl, it being possible for the above-mentioned radicals which contain C to be monosubstituted or polysubstituted by halogen or monosubstituted or disubstituted by $(C_1-C_6)$alkoxy, $(C_2-C_6)$alkenyloxy, $(C_2-C_6)$alkynyloxy, $(C_1-C_6)$alkylthio, $(C_1-C_6)$alkylsulfinyl, $(C_1-C_6)$alkylsulfonyl or $(C_1-C_6)$alkoxycarbonyl, or by phenyl which can be monosubstituted or polysubstituted by halogen, $(C_1-C_4)$alkyl, $(C_1-C_4)$alkoxy, $(C_1-C_4)$alkylthio, $(C_1-C_4)$alkoxycarbonyl or $NO_2$, it being furthermore possible for one of the two radicals $R^4$ to be phenyl which can be monosubstituted or polysubstituted by halogen, $(C_1-C_4)$alkyl, $(C_1-C_4)$alkoxy, $NO_2$ or $CF_3$, or for the two radicals $R^4$ together to be an alkylene radical $—(CH_2)_m—$;

the $R^5$ radicals independently of one another are H, or $(C_1-C_6)$alkyl which can be monosubstituted or polysubstituted by halogen or monosubstituted or disubstituted by $(C_1-C_6)$alkoxy, $(C_1-C_6)$alkylthio, $(C_1-C_6)$alkylsulfinyl or $(C_1-C_6)$alkoxycarbonyl, or it being possible for one of the radicals $R^5$ to be phenyl which can be monosubstituted or polysubstituted by halogen, $(C_1-C_4)$alkyl, $(C_1-C_4)$alkoxy, $NO_2$, $CF_3$ or $(C_1-C_6)$alkoxycarbonyl, or for the two radicals $R^5$ together to be an alkylene radical $-(CH_2)_n-$;

the $R^6$ radicals independently of one another are H, halogen, or $(C_1-C_6)$alkyl, $(C_1-C_6)$alkoxy or $(C_1-C_6)$alkylthio which can be monosubstituted or polysubstituted by halogen or monosubstituted or disubstituted by $(C_1-C_4)$alkoxy or $(C_1-C_4)$alkylthio; or are a radical $N(R^{11})_2$, $(C_3-C_6)$cycloalkyl, $-OCHR^7COOR^{11}$, $(C_3-C_5)$alkenyl, $(C_2-C_4)$alkynyl, $(C_3-C_5)$alkenyloxy or $(C_3-C_5)$alkynyloxy;

$R^7$ is H or $(C_1-C_4)$alkyl;

$R^8$ is $(C_1-C_4)$alkyl, $-CHF_2$ or $-CH_2CF_3$;

the $R^{11}$ radicals independently of one another are H, $(C_1-C_4)$alkyl, $(C_2-C_4)$alkenyl or $(C_3-C_4)$alkynyl;

X is O, S or $NR^{12}$;

Y is O or S;

$R^{12}$ is H, $(C_1-C_6)$alkyl, $(C_2-C_6)$alkenyl, $(C_2-C_6)$alkynyl, $(C_1-C_6)$alkoxy, or a radical of formula

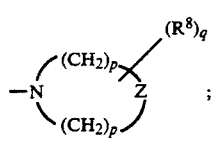

m is an integer from 2 to 6;
n is an integer from 3 to 6;
p is an integer from 1 to 3;
q is an integer from 0 to 3; and
Z is O, S, $CH_2$, NH or $N(C_1-C_4$-alkyl), or an agriculturally acceptable salt thereof and the remainder to 100% by weight of an inert auxiliary.

6. A method of controlling noxious plants which comprises applying an effective amount of a compound of formula I

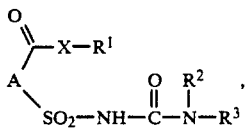

or a stereoisomer thereof, wherein:

A is a radical of formula $>C(R^4)_2$ or $>C=(R^5)_2$;

$R^1$ is H, $(C_1-C_8)$alkyl, $(C_2-C_8)$alkenyl, $(C_2-C_8)$alkynyl, it being possible for these aliphatic radicals to be monosubstituted or polysubstituted by halogen, or to be monosubstituted or disubstituted by $(C_1-C_6)$alkoxy, $(C_2-C_6)$alkenyloxy, $(C_2-C_6)$alkynyloxy, $(C_1-C_6)$alkylthio, $(C_1-C_6)$alkylsulfinyl, $(C_1-C_6)$alkylsulfonyl, $(C_1-C_6)$alkoxycarbonyl or by phenyl; or is $(C_3-C_8)$cycloalkyl which can be monosubstituted or polysubstituted by halogen, or monosubstituted or disubstituted by $(C_1-C_4)$alkoxy or $(C_1-C_4)$alkylthio; or is $(C_5-C_8)$cycloalkenyl, cyclopropylmethyl, epoxypropyl, furfuryl, tetrahydrofurfuryl, or phenoxy$(C_1-C_6)$alkyl or phenyl both of which can be substituted in the phenyl ring by halogen, $(C_1-C_4)$alkyl, $(C_1-C_4)$alkoxy or $NO_2$;

$R^2$ is H, $(C_1-C_8)$alkyl, $(C_2-C_8)$alkenyl, $(C_2-C_8)$alkynyl or $(C_1-C_4)$alkoxy;

$R^3$ is a radical of formula

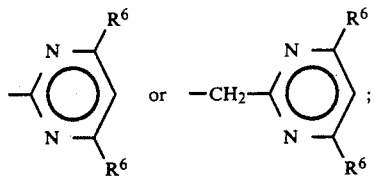

the $R^4$ radicals independently of one another are H, $(C_1-C_6)$alkyl, $(C_2-C_6)$alkenyl, $(C_2-C_6)$alkynyl, $(C_3-C_8)$cycloalkyl, it being possible for the above-mentioned radicals which contain C to be monosubstituted or polysubstituted by halogen or monosubstituted or disubstituted by $(C_1-C_6)$alkoxy, $(C_2-C_6)$alkenyloxy, $(C_2-C_6)$alkynyloxy, $(C_1-C_6)$alkylthio, $(C_1-C_6)$alkylsulfinyl, $(C_1-C_6)$alkylsulfonyl or $(C_1-C_6)$alkoxycarbonyl, or by phenyl which can be monosubstituted or polysubstituted by halogen, $(C_1-C_4)$alkyl, $(C_1-C_4)$alkoxy, $(C_1-C_4)$alkylthio, $(C_1-C_4)$alkoxycarbonyl or $NO_2$, it being furthermore possible for one of the two radicals $R^4$ to be phenyl which can be monosubstituted or polysubstituted by halogen, $(C_1-C_4)$alkyl, $(C_1-C_4)$alkoxy, $NO_2$ or $CF_3$, or for the two radicals $R^4$ together to be an alkylene radical $-(CH_2)_m-$;

the $R^5$ radicals independently of one another are H, or $(C_1-C_6)$alkyl which can be monosubstituted or polysubstituted by halogen or monosubstituted or disubstituted by $(C_1-C_6)$alkoxy, $(C_1-C_6)$alkylthio, $(C_1-C_6)$alkylsulfinyl or $(C_1-C_6)$alkoxycarbonyl, or it being possible for one of the radicals $R^5$ to be phenyl which can be monosubstituted or polysubstituted by halogen, $(C_1-C_4)$alkyl, $(C_1-C_4)$alkoxy, $NO_2$, $CF_3$ or $(C_1-C_6)$alkoxycarbonyl, or for the two radicals $R^5$ together to be an alkylene radical $-(CH_2)_n-$;

the $R^6$ radicals independently of one another are H, halogen, or $(C_1-C_6)$alkyl, $(C_1-C_6)$alkoxy or $(C_1-C_6)$alkylthio which can be monosubstituted or polysubstituted by halogen or monosubstituted or disubstituted by $(C_1-C_4)$alkoxy or $(C_1-C_4)$alkylthio; or are a radical $N(R^{11})_2$, $(C_3-C_6)$cycloalkyl, $-OCHR^7COOR^{11}$, $(C_3-C_5)$alkenyl, $(C_2-C_4)$alkynyl, $(C_3-C_5)$alkenyloxy or $(C_3-C_5)$alkynyloxy;

$R^7$ is H or $(C_1-C_4)$alkyl;

$R^8$ is $(C_1-C_4)$alkyl, $-CHF_2$ or $-CH_2CF_3$;

the $R^{11}$ radicals independently of one another are H, $(C_1-C_4)$alkyl, $(C_2-C_4)$alkenyl or $(C_3-C_4)$alkynyl;

X is O, S or $NR^{12}$;

Y is O or S;

$R^{12}$ is H, $(C_1-C_6)$alkyl, $(C_2-C_6)$alkenyl, $(C_2-C_6)$alkynyl, $(C_1-C_6)$alkoxy, or a radical of formula

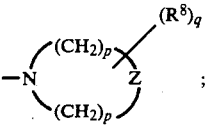

m is an integer from 2 to 6;
n is an integer from 3 to 6;
p is an integer from 1 to 3;
q is an integer from 0 to 3; and
Z is O, S, $CH_2$, NH or $N(C_1-C_4$-alkyl), or an agriculturally acceptable salt thereof to a noxious plant or to soil which is used in agriculture or industry.

* * * * *